United States Patent [19]
Houser et al.

[11] Patent Number: 6,149,681
[45] Date of Patent: *Nov. 21, 2000

[54] RADIALLY EXPANDING PROSTHESES AND SYSTEMS FOR THEIR DEPLOYMENT

[75] Inventors: Russell A. Houser, Livermore; James G. Whayne, Saratoga; Sid D. Fleischman, Menlo Park, all of Calif.

[73] Assignee: Converge Medical, Inc., Pleasanton, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/932,566

[22] Filed: Sep. 19, 1997

Related U.S. Application Data

[60] Provisional application No. 60/026,592, Sep. 20, 1996, and provisional application No. 60/044,625, Apr. 18, 1997.

[51] Int. Cl.$^7$ ........................................ A61F 2/00
[52] U.S. Cl. ............................................. 623/1.12
[58] Field of Search ...................... 623/1, 11, 12, 623/1.12; 606/194, 195

[56] References Cited

U.S. PATENT DOCUMENTS

| | | | |
|---|---|---|---|
| 4,877,030 | 10/1989 | Beck et al. | 606/195 |
| 5,078,736 | 1/1992 | Behl | 623/1 |
| 5,100,429 | 3/1992 | Sinofsky et al. | 606/195 |
| 5,123,917 | 6/1992 | Lee | 623/1 |
| 5,306,294 | 4/1994 | Winston et al. | 623/1 |
| 5,354,309 | 10/1994 | Schnepp-Pesch et al. | 606/198 |
| 5,383,926 | 1/1995 | Lock et al. | 623/1 |
| 5,405,322 | 4/1995 | Lennox et al. . | |

(List continued on next page.)

FOREIGN PATENT DOCUMENTS

| | | |
|---|---|---|
| WO 96/22745 | 8/1996 | WIPO . |
| WO 97/43961 | 11/1997 | WIPO . |
| WO 98/03118 | 1/1998 | WIPO . |
| WO 98/07399 | 2/1998 | WIPO . |
| WO 98/19608 | 5/1998 | WIPO .................. A61B 17/22 |
| WO 98/19618 | 5/1998 | WIPO .................. A61B 19/00 |
| WO 98/19629 | 5/1998 | WIPO .................. A61F 2/06 |
| WO 98/19630 | 5/1998 | WIPO .................. A61F 2/06 |
| WO 98/19631 | 5/1998 | WIPO .................. A61F 2/06 |
| WO 98/19632 | 5/1998 | WIPO .................. A61F 2/06 |
| WO 98/19634 | 5/1998 | WIPO .................. A61F 2/06 |
| WO 98/19635 | 5/1998 | WIPO .................. A61F 2/06 |
| WO 98/19636 | 5/1998 | WIPO .................. A61F 2/06 |
| WO 98/19732 | 5/1998 | WIPO .................. A61M 25/01 |

OTHER PUBLICATIONS

Cragg et al. (1982). "Endovascular Diathermic Vessel Occlusion," *Radiology*. 144: 303–308.

Gorisch et al. (1982). "Heat–Induced Contraction of Blood Vessels," *Lasers in Surgery and Medicine*. 2: 1–13.

Heijmen et al. (1999). "A Novel One–Shot Anastomotic Stapler Prototype for Coronary Bypass Grafting on the Beating Heart: Feasibility in the Pig," *J. Thorac Cardiovasc Surg*. 117: 117–125.

*Primary Examiner*—Michael J. Milano
*Attorney, Agent, or Firm*—Morrison & Foerster LLP

[57] ABSTRACT

A resilient graft construction incorporates a structural layer formed of a resilient body compatible metal or polymer, and a fluid impervious layer of graft material secured to the structural layer. The structural layer includes an elongate longitudinal primary section, and secondary sections extended transversely from opposite sides of the primary section. The secondary sections can be arranged in opposed pairs, or staggered. The secondary sections further can be tapered in width, thickness or both. The grafts can be constructed by stamping or otherwise severing structural layer patterns from a flat sheet of structural material, then thermally setting the structural layers when they are wrapped about a mandril to determine a relaxed-state curvature. Opposed longitudinal edges either can overlap one another or be spaced apart from one another in the relaxed state. According to one alternative, the structural layer alone functions as a stent. Other alternatives include circumferentially closed graft structures, one of which consists of a resilient graft material.

42 Claims, 15 Drawing Sheets

U.S. PATENT DOCUMENTS

| | | | |
|---|---|---|---|
| 5,411,550 | 5/1995 | Herweck et al. | 623/1 |
| 5,433,723 | 7/1995 | Lindenberg | 606/198 |
| 5,441,515 | 8/1995 | Khosravi et al. | 606/194 |
| 5,443,497 | 8/1995 | Venbrux . | |
| 5,540,713 | 7/1996 | Schnepp-Pesch et al. | 606/198 |
| 5,549,662 | 8/1996 | Fordenbacher | 623/1 |
| 5,618,301 | 4/1997 | Hauenstein et al. | 606/198 |
| 5,665,117 | 9/1997 | Rhodes . | |
| 5,707,386 | 1/1998 | Schnepp-Pesch et al. | 606/194 |
| 5,716,393 | 2/1998 | Lindenberg et al. | 623/1 |
| 5,733,327 | 3/1998 | Igaki | 623/1 |
| 5,755,775 | 5/1998 | Trerotola et al. . | |
| 5,931,842 | 8/1999 | Goldsteen et al. . | |
| 5,934,286 | 8/1999 | Maginot . | |
| 5,938,672 | 8/1999 | Nash . | |
| 5,938,696 | 8/1999 | Goicoechea et al. . | |
| 5,944,019 | 8/1999 | Knudson et al. . | |
| 5,944,730 | 8/1999 | Nobles et al. . | |
| 5,944,738 | 8/1999 | Amplatz et al. . | |
| 5,944,750 | 8/1999 | Tanner et al. . | |
| 5,957,940 | 9/1999 | Tanner et al. . | |
| 5,968,089 | 10/1999 | Krajíček . | |
| 5,972,017 | 10/1999 | Berg et al. . | |
| 5,976,178 | 11/1999 | Goldsteen et al. . | |
| 6,010,529 | 1/2000 | Herweck et al. . | |

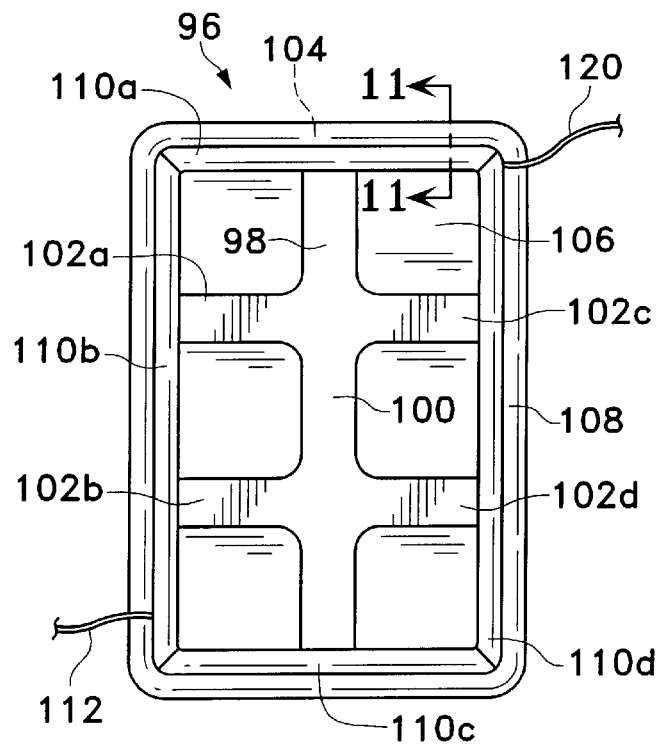
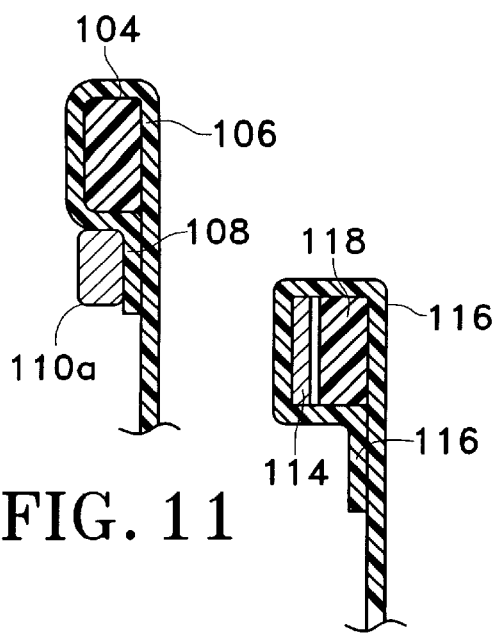
FIG. 10
FIG. 11
FIG. 12
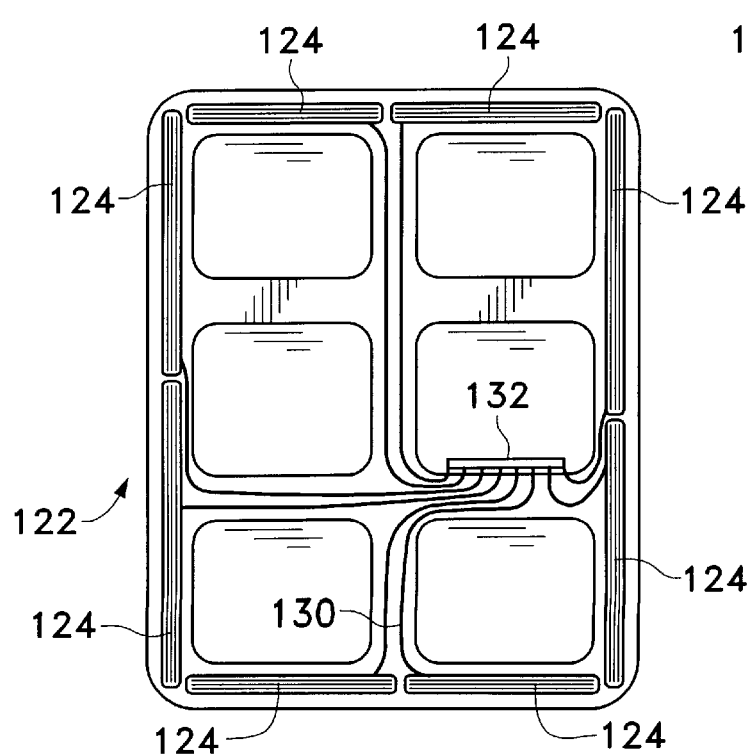
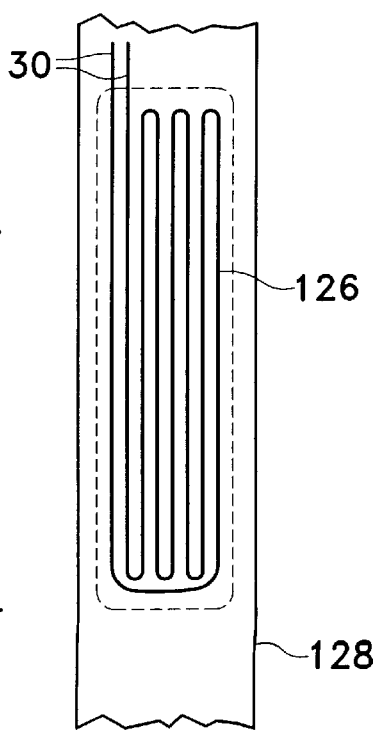
FIG. 13
FIG. 14

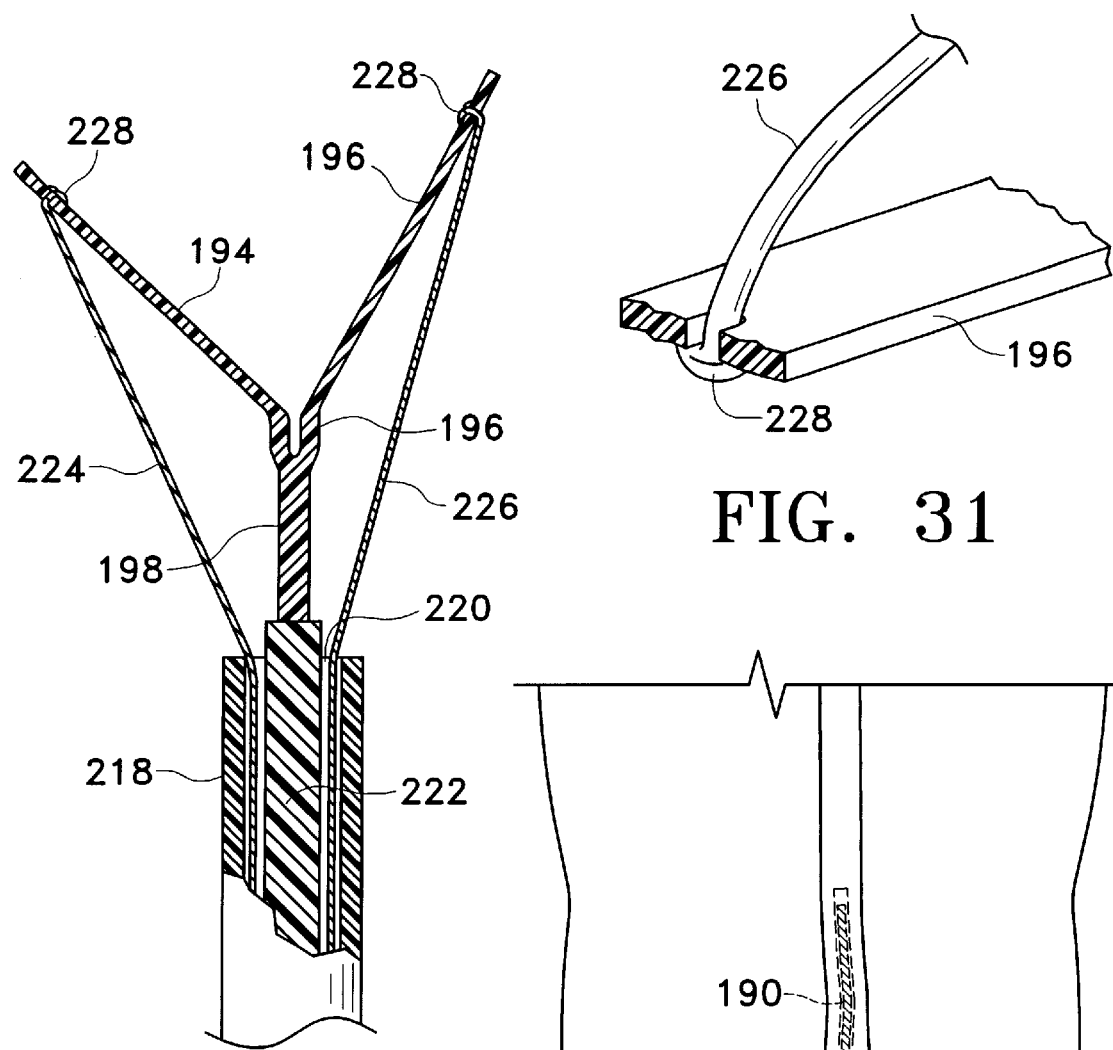
FIG. 31
FIG. 30
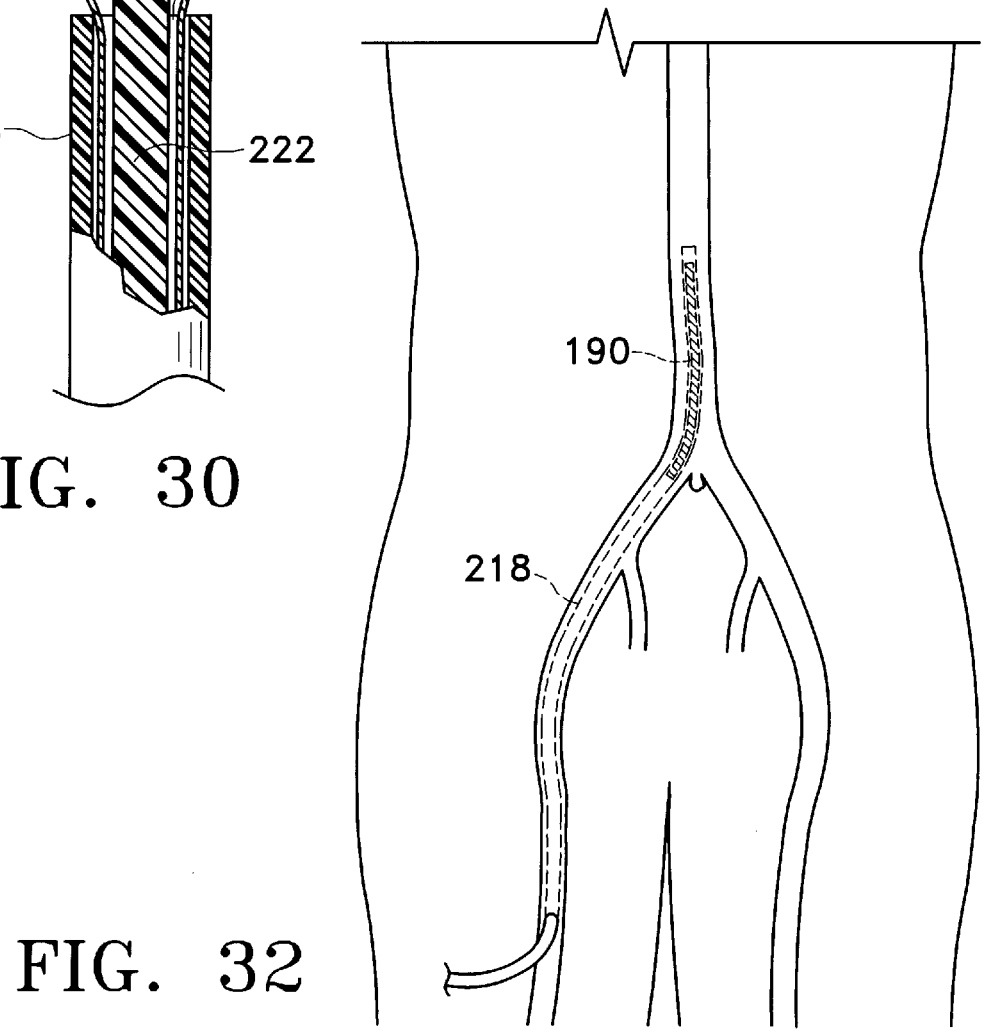
FIG. 32

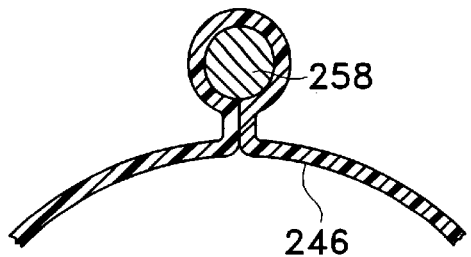
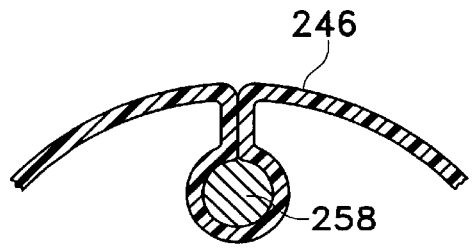
FIG. 39  FIG. 40
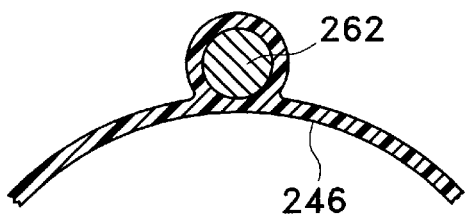
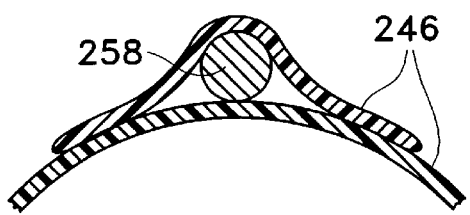
FIG. 41  FIG. 42
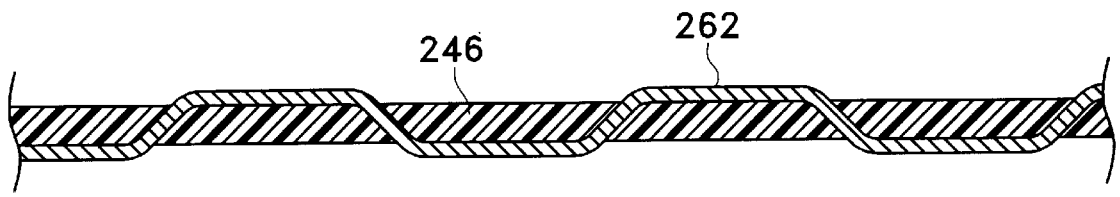
FIG. 43

RADIALLY EXPANDING PROSTHESES AND SYSTEMS FOR THEIR DEPLOYMENT

This application claims the benefit of: Provisional Application No. 60/026,592 entitled Self-Expanding Graft and Securing System, filed Sep. 20, 1996; and Provisional Application No. 60/044,625 entitled Additional Split Wall Graft Concepts and Grafts Which Target Branching Vessel Aneurysms, filed Apr. 18, 1997.

BACKGROUND OF THE INVENTION

The present invention relates to vascular prosthetic devices such as grafts and stents, especially of the elastic type that can be compressed to a reduced radius for delivery. The invention further concerns systems for delivering the prostheses to their intended intralumenal treatment sites, and means for securing the prostheses at their respective sites.

The vascular graft is a useful device for treating aneurysms and other blood vessel abnormalities. Common aneurysms result from weak blood vessel walls that typically balloon outward from the intrinsic pressure in the vessel. Aneurysms can apply pressure on adjacent anatomic structures producing abnormal functions. Also, the affected vessels have a potential to split and rupture, thus causing internal bleeding and potentially life-threatening conditions. In addition to common aneurysms, dissecting aneurysms involve a fissure in the internal wall of the vessel. Blood flows through the fissure and can collect between the internal wall and the outer wall, causing the vessel wall to swell.

A vascular graft can isolate an aneurysm or other blood vessel abnormality from the blood pool, reducing pressure on the weak vessel wall. The graft also can reduce blood loss, should the vessel rupture. Ideally, the graft provides reinforcement at the weakened part of the vessel, reduces pressure on the vessel wall, and minimizes blood flow into the space between the graft and the aneurysm while allowing blood flow through an internal lumen of the graft without the formation of thrombus. The graft should remain secured in place, despite the pulsations of the vessel due to the pumping action of the heart.

To isolate aneurysms, physicians have surgically removed them and sutured graft material in place. Attempts to percutaneously insert and place grafts into target vessels have involved grafts made of an inelastic textile, fixed through the use of hooks or expandable stents. Delivering and deploying such grafts typically involves a catheter or other device to carry the graft to the target vessel and to the treatment site within the target vessel. Then, a balloon is inflated to expand the graft and attachment structures. Usually the physician must inflate and deflate the balloon repeatedly to expand the graft without continuously occluding the vessel. The inflation/deflation cycles can weaken the balloon. Such grafts frequently experience leaks between the graft and the blood vessel wall. The attachment structures are susceptible to fatigue failure. Frequently, there is less than the desired degree of contiguous contact of a graft material with the blood vessel interior wall. Such contact is desirable, because the graft textiles are potentially thrombogenic due to their rough weave, and contact thus promotes healing of the aneurysm by forming a thin cellular layer between the vessel and the graft.

The required delivery systems are cumbersome in their manufacture and use. More particularly, the need for balloons requires assurance that each balloon has an adequate burst strength to withstand pressures required to enlarge the graft and attach the graft support structures to the vessel wall. Single chamber balloons occlude the vessel wall when they are expanded. Moreover, balloon inflation has the potential to overexpand the vessel wall, which can cause endothelial cracking, promote restenosis or even rupture the vessel. Also, whenever the balloon is deflated before the graft is secured to the vessel wall, there is a risk that blood flow will shift the graft axially away from its intended location. Finally, conventional grafts must be provided in many different sizes, since each graft is limited as to the range of blood vessel diameters that it can accommodate.

Another type of intravascular prosthesis is the radially expandable stent, frequently used to counteract restenosis of a vessel following a translumenal angioplasty procedure. Typically, balloons are used to open the vessel wall and to expand the stent. Size and burst pressure considerations limit the efficacy of balloons in expanding the stent. Often, multiple balloons are required to expand a single stent, due to the tendency of balloons to burst during stent expansion.

A frequently encountered problem is an aneurysm or other abnormality in a branched vessel. Prosthesis with corresponding junctions, frequently called "Y" grafts, have been used to isolate such abnormalities from the blood flow. Such grafts, which typically involve several tubular structures, are difficult to deploy and secure at the intended treatment site, requiring either maneuvering of a preassembled graft in opposite axial directions, insertion of a tubular structure into another after their approximate placement, or both.

Therefore, it is an object of the present invention to provide an implantable prosthesis formable into a reduced-radius profile to facilitate its delivery to a site of intralumenal implantation, then radially enlargeable at the site without balloons or other devices.

Another object is to provide a more effective fixation of an implantable prosthesis within a body lumen, and in connection with grafts a more effective seal against leakage.

A further object is to provide an improved system for deploying prostheses, preferably enabling retraction of a partially deployed prosthesis for repositioning along a lumen if desired.

Yet another object is to provide an implantable prosthesis that is easier to deploy within branched vessels and more effectively fluid-isolates aneurysms and other abnormalities occurring in branched vessels.

SUMMARY OF THE INVENTION

To achieve the above and other objects, there is provided an intralumenally implantable prosthesis. The prosthesis has a structural layer including an elongate primary section extended in a longitudinal direction. A plurality of secondary sections extend substantially transversally from the primary section and are curved about an axis substantially parallel to the primary section. Consequently the structural layer, when in a relaxed state (i.e., when not subject to external forces), conforms to a cylindrical shape and has a predetermined radius. The secondary sections further are adapted to allow a radial compression of the structural layer to a reduced-radius delivery profile responsive to an external force. When the external force is removed, the structural layer tends to return to the relaxed state.

Preferably, each of the secondary sections converges, either in its width or in its thickness in a direction from a first end of the segment adjacent to the primary segment toward a second and opposite end. This allows a variance in the amount of restoring force along the length of each secondary segment under radial compression. It likewise allows variance in the restoring force along each secondary section of an implanted prosthesis.

There are several suitable arrangements for the secondary sections. A particularly preferred arrangement involves secondary sections extending from opposite sides of the primary section, in the manner that ribs extend from the backbone to form the ribcage. Opposed sections can have free ends spaced apart from one another as in a rib cage. Alternatively, the free ends of opposed secondary sections or "ribs" can overlap one another when the structural layer is in the relaxed state. In another alternative, the secondary sections can be staggered, so that they do not contact one another in either the relaxed or radially compressed states, even when long enough to overlap.

In some embodiments, the structural layer supports a substantially continuous and compliant graft layer, which tends to conform to the shape of the structural layer and is substantially impervious to blood and other body fluids. The result is a graft suitable for isolating an aneurysm or other vessel abnormality from the blood flow. The grafts, consistent with the secondary section arrangements just discussed, can be overlapping (i.e., in a closed or tubular form), or open to provide spaced apart axial edges. Usually, the closed grafts are better suited for common aneurysms. Where the aneurysm affects less than the full circumference of a vessel, as often is the case with dissecting aneurysms, the open graft structure affords the option of isolating the abnormality and at the same time maintaining patency of an adjacent branch vessel.

According to a further aspect of the invention, the prostheses can be manufactured by stamping multiple forms—typically one for each prosthesis—from a flat sheet of the structural material. Each form incorporates at least an axial primary section and several secondary sections., thus to provide the prosthesis structural layer. Each form is wrapped about a cylindrical mandrel with its primary section parallel to the mandrel axis, then heated to a temperature sufficient to set the structural layer in the profile determined by the mandrel, which is the predetermined relaxed-state profile. Typically, a circular cylindrical mandrel is used to provide a uniform radius for the structural layer. Alternatively, the mandrel can be tapered or otherwise modified as desired, to provide non-uniform radii over the prosthesis length.

The fabrication of a graft involves the additional step of securing at least one layer of graft material to the structural layer, either before or after the structural layer has been shaped. If desired, a second layer of the graft material is secured to the structural layer. The pair of graft layers can further insure isolation of the blood vessel abnormality, and can be used in concert to provide pockets for containing a drug solution for diffusion into the tissue wall segment after deployment. The pockets also can contain a biocompatible foam that cures and solidifies after deployment of the prosthesis, to provide added structural integrity.

Another aspect of the present invention is a process for implanting a prosthesis at a selected treatment site within a body lumen, including the following steps:

a. using an elongate and flexible prosthesis delivery device with a distal end adapted to releasably support a prosthesis, to introduce a prosthesis into a body lumen and to convey the prosthesis to an intended treatment site within the body lumen, while maintaining the proximal end of the device outside of the body;

b. with the prosthesis positioned at the intended treatment site, releasing the prosthesis from the delivery device to allow the prosthesis to radially expand into contact with surrounding tissue;

c. while the prosthesis is in contact with the surrounding tissue, heating at least a portion of the surrounding tissue near the implantable prosthesis, to bond the prosthesis to the surrounding tissue at least proximate said portion of the tissue; and d. proximally withdrawing the device from the lumen, to leave the prosthesis at the intended treatment site.

One particularly advantageous form of heating is with electrically conductive heating elements, either as part of or in addition to the prosthesis support structure. In either event, heating is accomplished by providing an electrical current to the heating elements. One approach involves coupling the heating elements to an radio frequency RF power source. A ground electrode also is coupled to power source, and positioned in close, spaced apart relation to heating elements. Providing current then results in ohmic heating of adjacent tissue. Alternatively, the electrodes can be resistively heated, thus to heat surrounding tissue for a thermal bond.

Another aspect of the invention is a system for deploying the prosthesis. One suitable option is an elongate catheter with a lumen at least at its distal end for containing the prosthesis in the reduced-radius delivery state. Deployment is accomplished either by moving the prosthesis distally beyond the catheter, or maintaining the prosthesis axially fixed while proximally retracting the catheter.

According to another option, two elongate stylets, axially movable relative to one another, are coupled respectively to opposite ends of the prosthesis. Manipulation of the stylets thus can either bring the prosthesis ends axially closer for radial expansion, or axially elongate the prosthesis to radially contract it. This option is suited to prostheses that axially elongate as they radially contract.

Thus, in accordance with the present invention, an implantable prosthesis can be compressed to a reduced-radius profile to facilitate delivery to a target site, then upon release resiliently radially enlarge into intimate contact with surrounding tissue, to achieve fixation at the site without hooks or other auxiliary fixing devices. The backbone-and-rib configuration lends itself well to a tailoring of the secondary sections or ribs, both as to their location and their profiles, facilitating designs that afford non-uniform distributions of elastic restoring force when the prostheses are radially compressed. This configuration also results in a unique "Y" graft, more easily implanted along branched vessels and more effectively isolating aneurysms at the junctions of branched vessels. Further, the prosthesis structural layer, either by its own electrical conductively or by its support of electrically conductive heating elements, enables formation of a thermal bond with tissue surrounding the prosthesis, to provide a more secure fixation of the prosthesis at the treatment site.

IN THE DRAWINGS

For a further understanding of the above and other features and advantages, reference is made to the following detailed description and to the drawings, in which:

FIG. 10 is a plan view of another alternative graft, shown uncoiled in a flat configuration to reveal electrical heating elements;

FIG. 11 is a sectional view taken along the line 11—11 in FIG. 10;

FIG. 12 is a sectional view similar to that of FIG. 11, showing an alternative construction;

FIG. 13 is a plan view of another alternative embodiment graft uncoiled in a flat configuration;

FIG. 14 is a more detailed illustration of a portion of FIG. 13;

FIG. 30 is a side sectional view of a further alternative bifurcated graft;

FIG. 31 is a perspective view showing a support member and pull wire of the graft in FIG. 30;

FIG. 32 illustrates deployment of the graft to FIG. 30 in a branched vessel;

FIGS. 39–43 illustrate alternative approaches for securing graft material to a support structure for the graft of FIG. 35;

Figure 37:
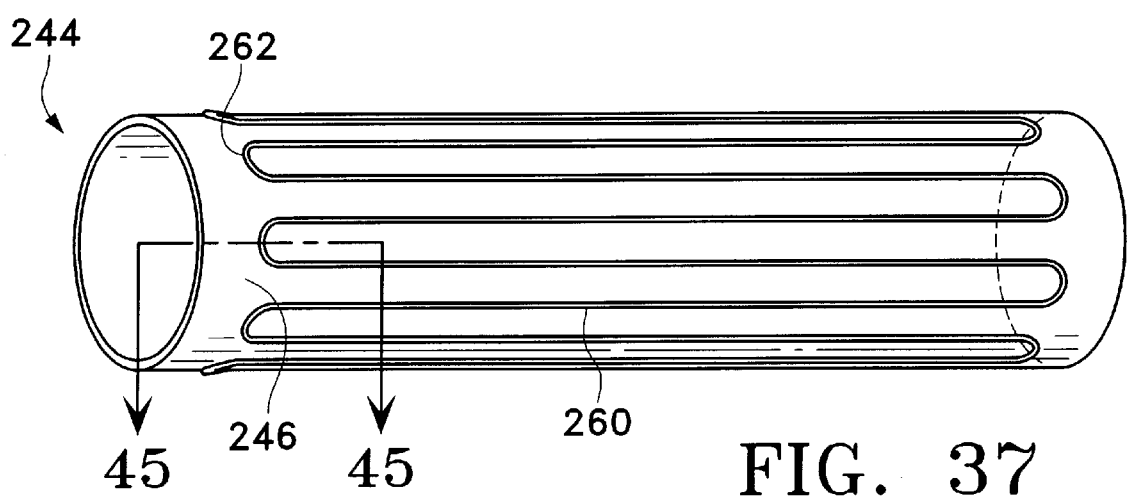
Figure 45:
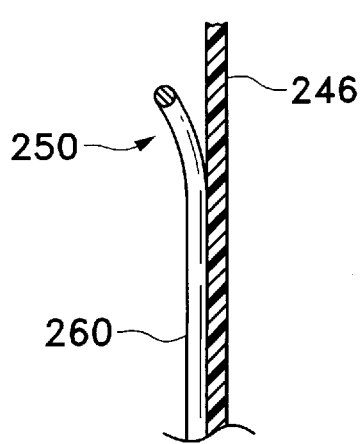
Figure 46:
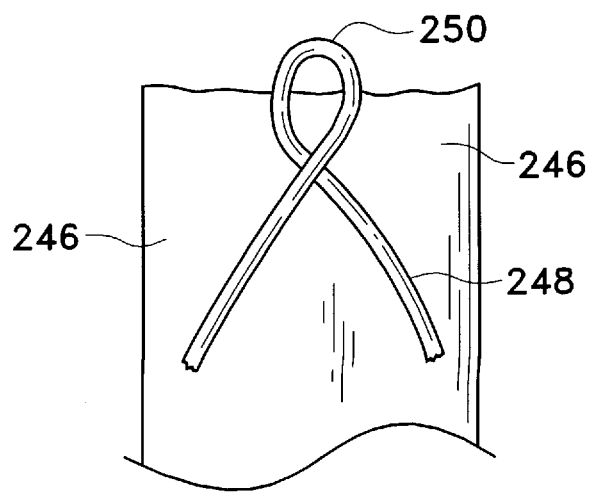
Figure 47:
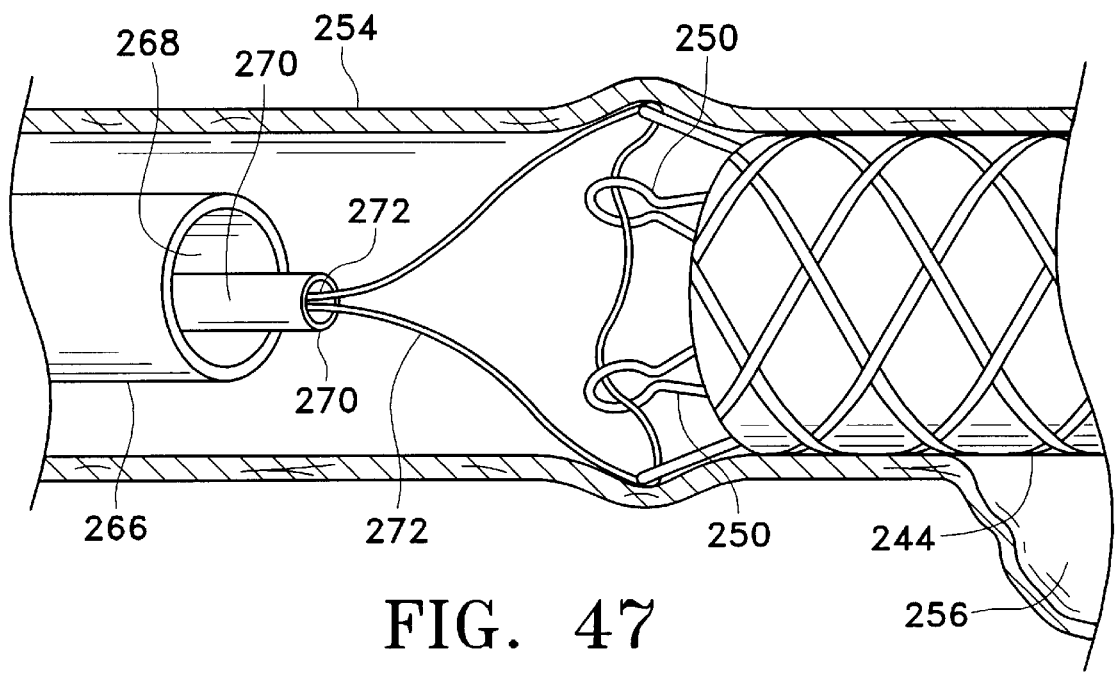
Figure 48:
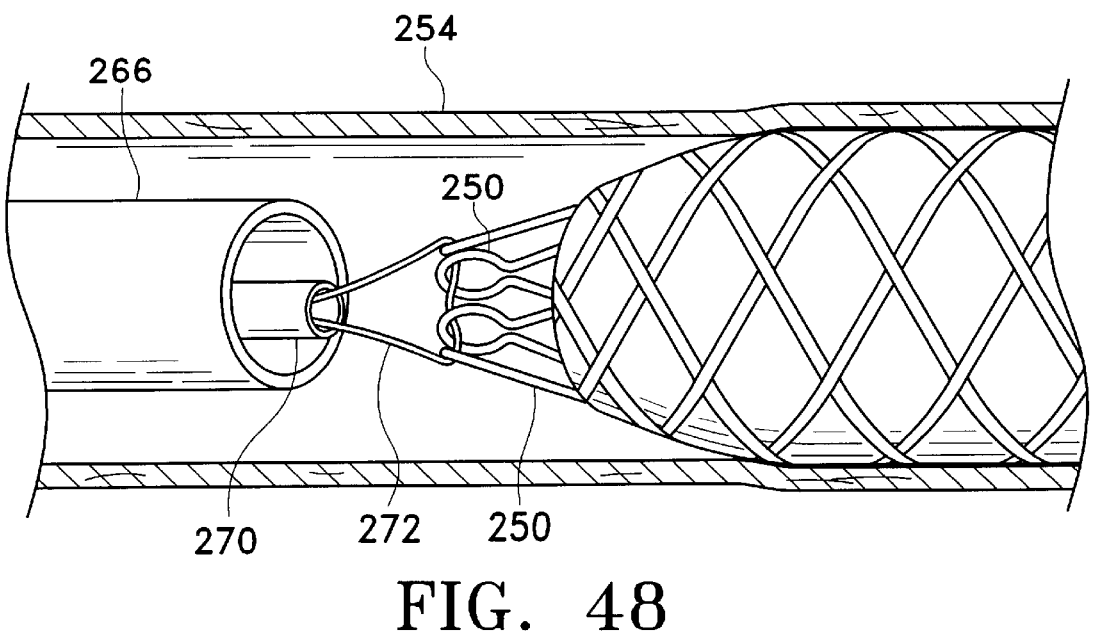
Figures 49, 50:
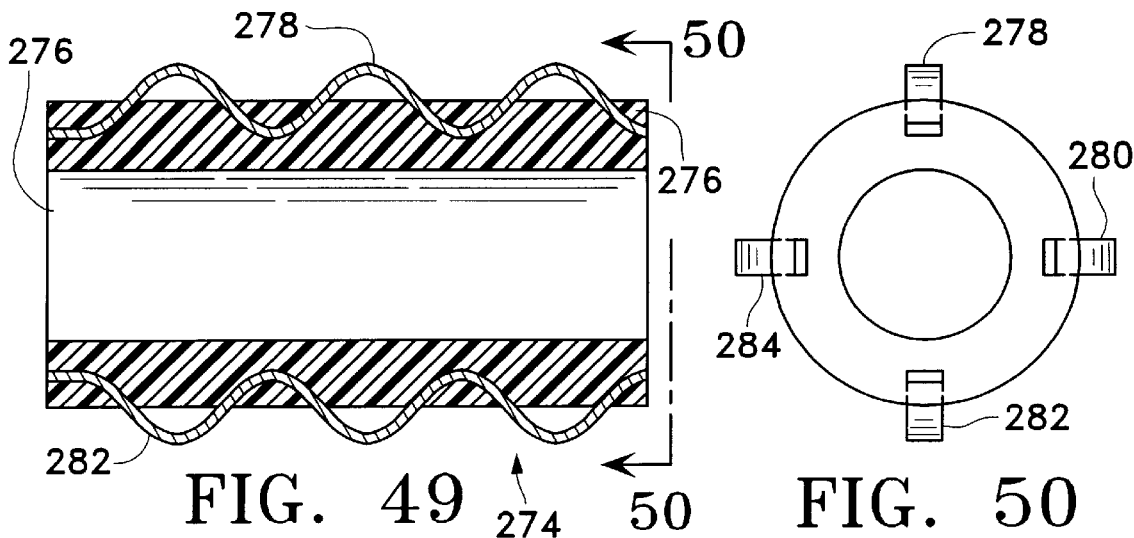
Figure 51:
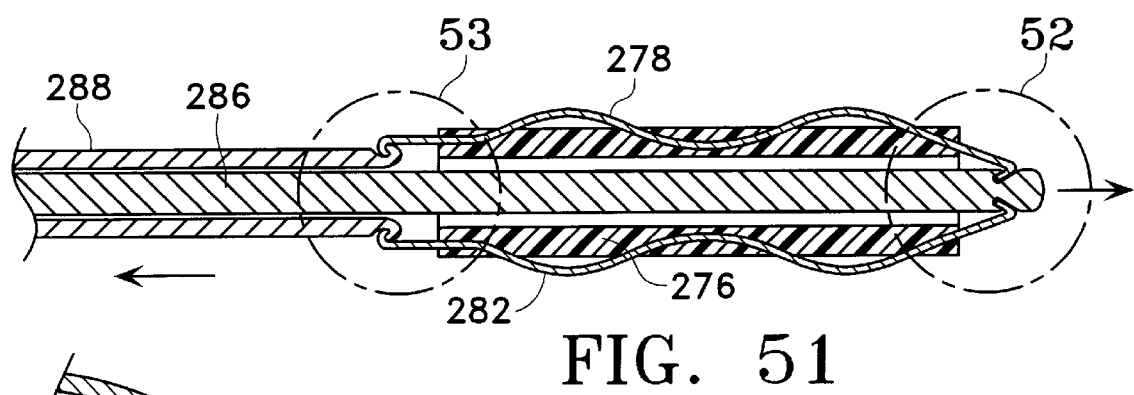
Figure 52:
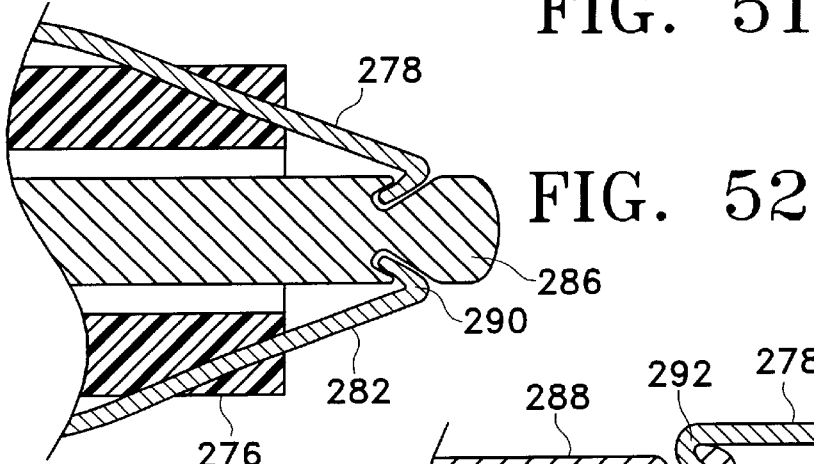
Figure 53:
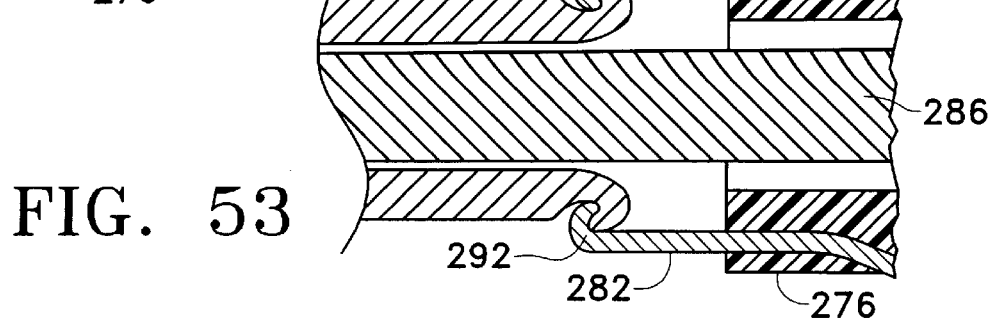
Figure 54:
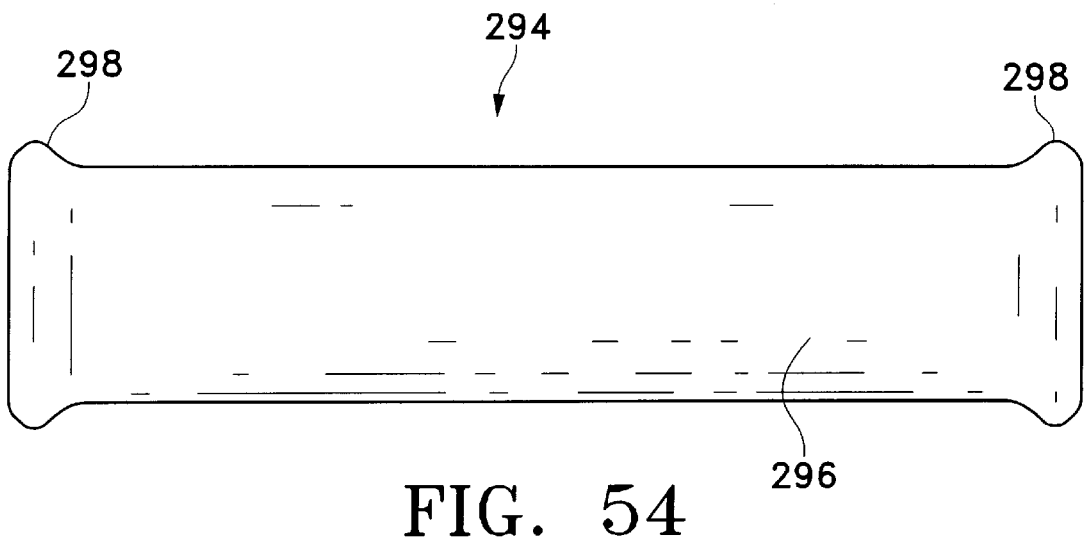
Figure 55:
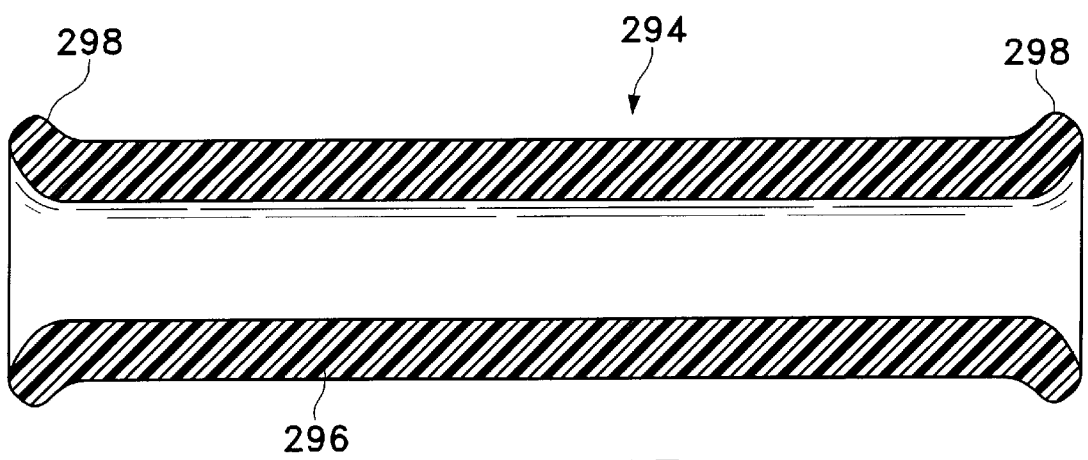

FIGS. 44a–d illustrate alternative support member end constructions;

FIG. 45 is a sectional view taken along the line 45—45 in FIG. 37;

FIG. 46 illustrates one of the alternative end constructions and a portion of the graft;

FIGS. 47 and 48 illustrate another embodiment graft and a system for deploying the graft;

FIG. 49 illustrates a further embodiment graft;

FIG. 50 is an end view of the graft shown in FIG. 49;

FIG. 51 illustrates a portion of a system for deploying the graft;

FIGS. 52 and 53 are more detailed views of portions of FIG. 51;

FIG. 54 illustrates another alternative embodiment graft construction;

FIG. 55 illustrates the graft in section; and

Figure 56:
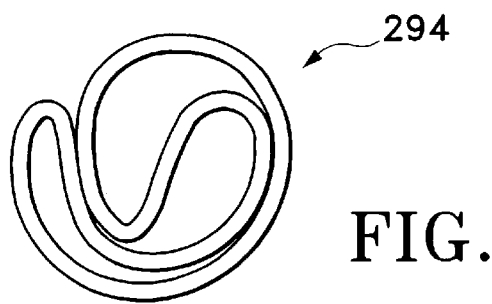

FIG. 56 is an end view showing the graft in a collapsed configuration for deployment.

DETAILED DESCRIPTION OF THE PREFERRED EMBODIMENTS

Figure 1:
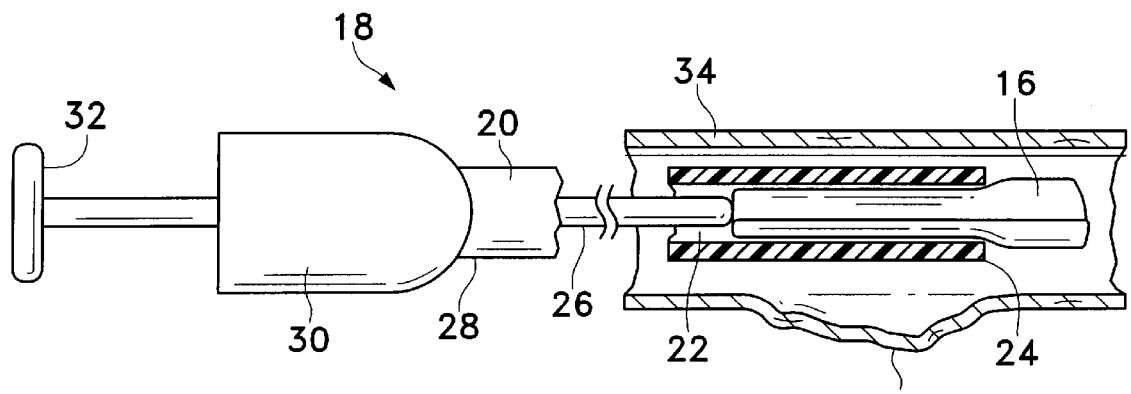
FIG. 1 is a side elevation, partially sectioned, showing a graft constructed according to the invention and a system for deploying the graft within a blood vessel.
Figure 2:
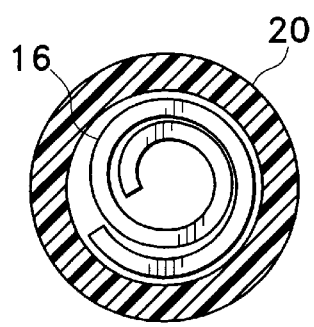
FIG. 2 is an end view showing the graft constrained within a catheter of the system.

Turning now to the drawings, there is shown in FIG. 1 an implantable vascular graft 16 and a system 18 for deploying the graft. System 18 includes an elongate flexible catheter 20 with a lumen 22 that runs the length of the catheter. Graft 16 is contained within the lumen at a distal end 24 of the catheter. Also contained within the catheter is a stylet 26, which has bending flexibility but is sufficiently stiff in the axial direction to apply an axial pushing force against the graft. At its proximal end 28, catheter 20 is coupled to a housing 30. Stylet 26 extends through the housing to a handle 32. By axially sliding handle 32 relative to the housing, an operator can move the stylet axially relative to the catheter, thus to push graft 16 distally relative to catheter 20.

With the proximal end of the catheter and the housing remaining outside of the body, catheter 20, with graft 16 radially compressed and contained within lumen 22, is guided interlumenally until the catheter distal end and graft are positioned near an intended treatment site, e.g., within a blood vessel 34 where an aneurysm 36 has formed.

When contained in the catheter lumen, graft 16 is coiled or wound in the form of a scroll, in a reduced-radius delivery profile. An elastic restoring force urges the graft to radially expand, but catheter 20 constrains the graft against radial expansion.

Figure 3:
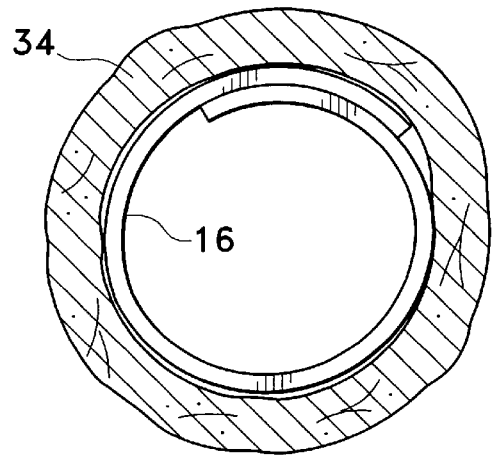
FIG. 3 is an end view showing the graft radially expanded into contact with surrounding tissue of the blood vessel.

Graft 16 is deployed by moving it axially beyond catheter 20. Moving handle 32 moves stylet 26 distally against the graft, moving the graft distally, eventually freeing the graft from catheter 20. As the graft becomes free of the catheter, it expands radially under its restoring force, until it engages vessel 34 as illustrated in FIG. 3. The graft is substantially uncoiled from its previous scroll-like profile, although a substantial overlap remains.

Figure 4:
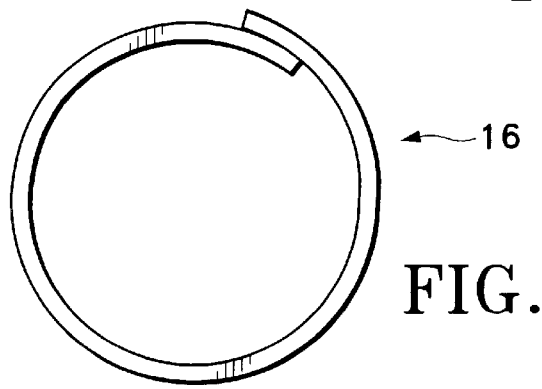
FIG. 4 is an end view of the graft in a relaxed state.

In FIG. 4, graft 16 is shown in its relaxed state, i.e. with no external radial forces applied to the graft. There is a slight overlapping of the axial end portions, although less than the overlap as shown in FIG. 3. Thus in FIG. 3, there is an equilibrium between an elastic restoring force in the graft (less than when the graft is wound tightly), and a counteracting radial force exerted by the tissue wall of blood vessel 34. These counteracting forces secure graft 16 within vessel 34, so that no hooks or other extraneous securing means are required.

Figure 5:
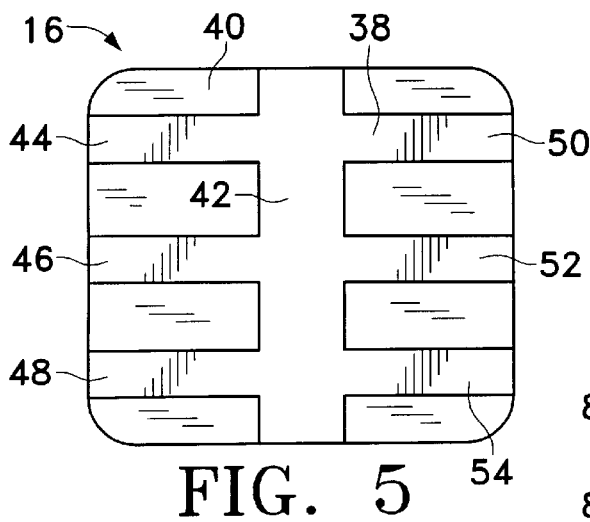
FIG. 5 is a plan view of the graft, uncoiled in a planar configuration.

In FIG. 5, graft 16 is shown completely unwound to a flat, planar configuration, to more clearly show its two-layered construction. The graft includes a structural layer 38, which is the top layer as shown in FIG. 5 and the inside layer when the graft is coiled into its tubular form. The other layer is a graft material layer 40. The graft material layer is compliant, tending to conform to the shape of structural layer 38. The graft layer also is substantially impervious to blood or other body fluids, either being nonporous or of sufficiently low porosity to prevent the passage of blood through it. Thus, when deployed in tubular form along blood vessel 34, graft 16 shunts blood past the aneurysm, i.e. the graft isolates aneurysm 36 from the blood flow.

Structural layer 38 is formed as a support frame with a primary section 42 extending longitudinally or axially (vertically as viewed in FIG. 5). A plurality of secondary sections 44, 46, 48, 50, 52 and 54 extend transversely from the primary section, arranged in opposed pairs. When the graft is coiled in its relaxed state as in FIG. 4, the primary and secondary sections can be likened to a rib cage, with the arcuate secondary "ribs" extending from the primary "backbone."

Structural layer 20 may be constructed from memory elastic material (such as nickel titanium), spring stainless steel, thermoset plastic, or other metal or polymeric material. The structural layer can be inherently radiopaque as when formed of certain metals, or may be doped with radiopaque materials such as barium or bismuth.

The primary section and secondary sections can be separate members, bonded together by spot welding or other suitable methods into the desired rib cage configuration. More preferably, the primary and secondary sections are of single-piece construction, stamped from a sheet of the selected structural material. As alternatives, a masking and chemical etching process can be used to form single-piece structural layers; or, a laser or water jet can be employed to mill or cut structural layers from the sheet material, with the water jet being suitable primarily for polymeric sheeting. In any event, multiple structural layers conforming to a predetermined pattern are severed from the sheet of structural material, which can have a thickness of e.g. about 5 miles (0.125 mm). To achieve the desired tubular configuration in the relaxed state, the structural layer can be wrapped about a cylindrical mandril having the desired radius, with primary section 42 parallel to the mandril longitudinal axis. Then, with the structural layer wound about the mandril, heat is applied, for example by heating the mandril, in a sufficient amount to thermally set the structural layer. The structural layer, which then tends to assume the relaxed state illustrated in FIG. 4, is allowed to cool, at which point a layer of graft material can be cut to the appropriate size and secured to the structural layer.

Graft material layer 40 can consist of a woven textile with a porosity (total open area divided by the total surface area) and pore size selected to limit the flow of blood through the graft material. Polyester (DACRON), nylon, and other biocompatible materials whose strands may be woven into a sheet are preferred. The graft material layer can be manufactured of extruded, blow molded, or dipped polymers such as PTFE, urethane, polyimide, nylon, silicone, polyethylene, or a combination of these materials.

The graft material layer is bonded to the structural layer, e.g., using adhesives, thermal bonding, sewing of a folded graft material layer or several layers, or other suitable means. While in some cases the graft material layer can be attached to a flat structural layer before thermal shaping, it frequently is necessary to thermally shape the structural layer before attaching the graft material, due to the high temperatures required for thermal shaping, particularly in the case of metal structural layers.

Certain vascular treatments do not require a prosthesis impervious to body fluids, although they do require maintaining the patency of a vessel. Stents are frequently suited for such applications. The above-described graft fabrication method is suitable for forming prostheses to meet these applications, more particularly by forming structural layers without attaching graft material layers. The result is a rib cage "stent" suitable for and maintaining vessel patency.

Figure 6:
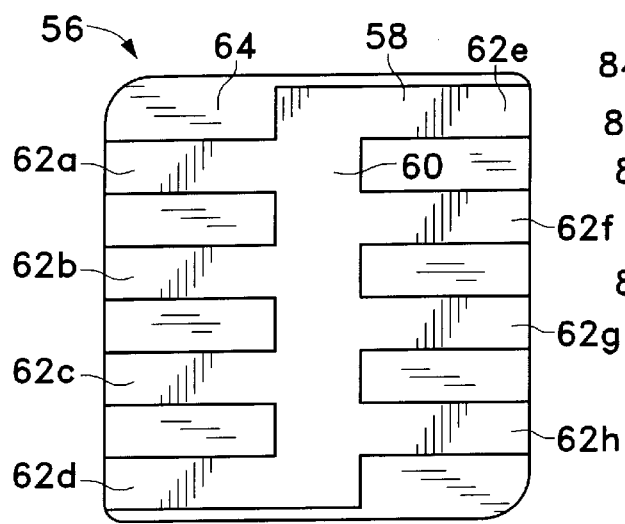
FIG. 6 is a plan view of an alternative embodiment graft, uncoiled to a planar configuration.

In narrower vessels, the need to minimize graft diameter becomes more critical, and the increased thickness along the overlapping end regions may present a problem. To address this problem, a graft 56 (FIG. 6) is formed with a structural layer 58 with a primary section 60 and transverse secondary sections 62a–62h that are staggered rather than in opposed pairs. A graft material layer 64 is secured to the structural layer. Due to the staggering of the secondary sections, there is no overlap of secondary sections, although opposed portions of the graft material do overlap.

Figure 7:
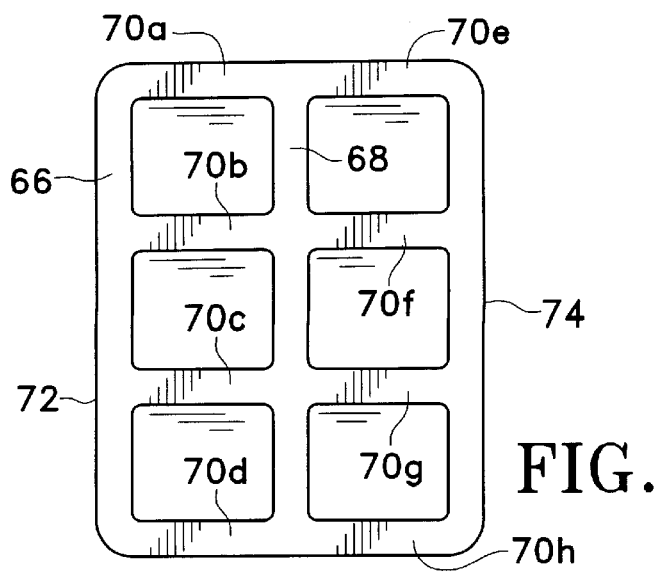
FIG. 7 is a plan view of an alternative graft support structure, uncoiled to a planar configuration.

Further, according to the present invention, the structural layer can be fabricated in different forms to meet a variety of needs for stents and graphs. For example, FIG. 7 shows a structural layer 66 including an axially extending primary section 68, secondary sections 70a–70h extending in opposite directions from the primary section, and opposed axially extending end sections 72 and 74. End sections 72 and 74, joined to what in previous embodiments are the free ends of the secondary sections, lends stability and more positively causes the secondary sections to conform to one another in their curvature. Structural layer 66 can be thermally shaped to a desired tubular profile as previously described to provide a stent, or shaped and joined with one or more layers of graft material to provide a graft.

Figure 8:
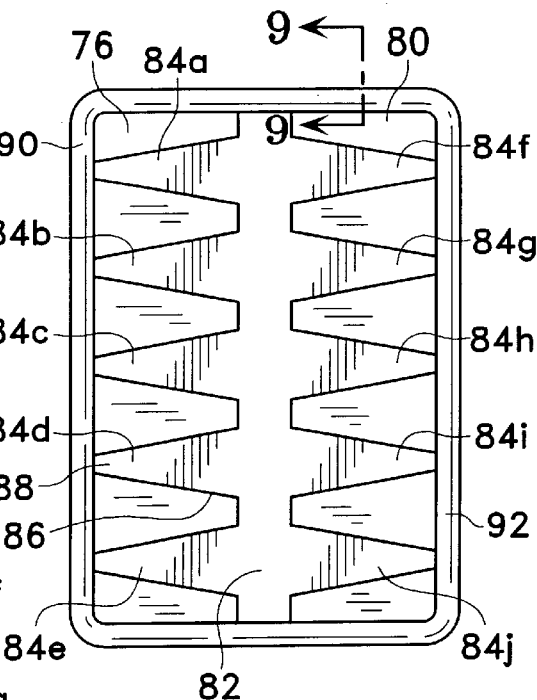
FIG. 8 is a plan view of another alternative graft in a planar configuration.

FIG. 8 shows a graft 76 composed of a structural layer 78 and an attached graft material layer 80. The structural layer includes an axial primary section 82, and tapered secondary sections or ribs 84a–84j arranged in opposed pairs of ribs. Each rib converges in its width in the transversely outward direction, i.e. in the direction from a base 86 at the primary section to an outward end 88. The structural layer further includes a rectangular outer frame 90 including a pair of outward axial sections and an opposed pair of nontapered transverse sections.

Figure 9:
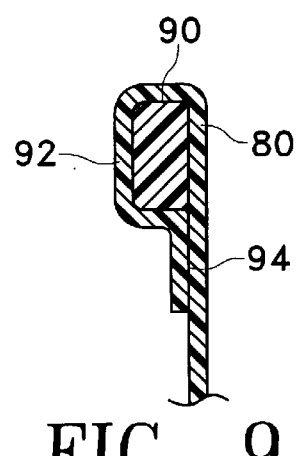
FIG. 9 is a sectional view taken along the line 9—9 in FIG. 8.

Graft material layer 80, generally behind the structural layer as viewed in FIG. 8, includes a portion 92 that is folded over and covers rectangular frame 90. Portion 92 is secured to the remainder of the graft material layer, to facilitate securing the graft material to the structural layer. As seen in FIG. 9, portion 92 can be bonded with an adhesive as indicated at 94. Thermal bonding and stitching of the graft fabric are suitable alternatives for attaching the graft material.

As an alternative, secondary sections 84 can be tapered in thickness, in lieu of or in addition to the taper in width. In either event, the result is that the restoring force in the secondary members is not uniform, but rather behaves according to a force gradient determined by the change in the profile of the secondary member. For example, in the graft of FIG. 8, in which the secondary sections converge in the direction away from the primary section, the elastic restoring force is diminished in that direction.

A variety of alternative rib cage arrangements can be employed. According to one variation, the secondary sections of the structural layer do not extend linearly in the transverse direction For example, the secondary sections or ribs can be parallel to one another, each including a first segment next to the primary section and extended from the primary section at an inclined angle, and a second segment extended from the first segment at an opposite inclined angle, each rib thereby resembling the letter "V." The ribs can have curves or other nonlinear features, so long as there is at least a general transverse extension away from the primary section.

FIG. 10 illustrates a graft 96 including a structural layer 98 with a longitudinal primary section 100, several untapered secondary sections 102a–102d, and a rectangular frame 104 surrounding the primary and secondary sections. An adjacent graft material layer 106 includes a portion 108 folded over and surrounding the rectangular frame and secured to the remaining graft material as previously described. Graft 96 also includes a rectangular heating element in the form of a series of elongate electrode strips 110a–110d bonded to the graft material. A conductive wire 112 couples the heating element to an RF current source (not shown). The current source provides an electrical current to the heating element, which in conjunction with a ground or indifferent electrode (not shown) enables ohmic heating of tissue adjacent the heating element. As seen in FIG. 11, the electrode strips are positioned inside the structural layer, and when the graft is formed into its tubular shape, are flush with the side of the structural layer facing the vessel wall. Thus, the heating element is positioned to prevent loss of coagulun or thrombi outside the graft into the vessel lumen as the graft is secured. This position also enhances contact between the electrode strips and the vessel wall.

An alternative position for the electrode strips is shown in FIG. 12, a sectional view similar to FIG. 11. In this position, the electrode strips 114 are contained between the graft material 116 and an outer rectangular frame 118 of the structural layer facing the vessel wall. This location is preferred when the heating element is a resistive wire, which heats surrounding tissue when current is transmitted through the element. Resistive heating requires an additional signal wire, shown at 120 in FIG. 10. Signal wires 112 and 120 may be spot welded or secured with an interference fit to provide an electrical circuit to deliver RF or direct current (DC) energy.

The purpose of the heating element is to thermally secure graft 96 to the vessel wall after its deployment. The electrode strips may be formed of platinum, platinum-iridium, stainless steel, or gold, and may be threaded through the graft material radially, with a larger surface area exposed to the exterior surface of the graft. Alternatively, the electrode strips are bonded to the graft material on the exterior surface. Regardless of whether RF energy or a direct current is provided, the heating element heats surrounding and adjacent tissue of the blood vessel, thus thermally fusing the graft edges to the vessel walls. As a result, the fixation of the graft is improved, and the graft is better able to withstand pressure fluctuations due to pumping of the heart without becoming dislodged from the implant site.

Thermal bonding is accompanied by an increase in impedance as a result of the formation of coagulum on the electrode which tends to attach the electrode to the vessel wall. The impedance increase can be used to detect such coagulation, and thus to detect thermal bonding of the graft to the vessel wall. For example, when the impedance increases beyond a threshold amount, e.g., 100 ohms above baseline, the graft is considered fused. Alternatively, temperature sensors can be employed to detect sealing. This is accomplished by forming a thermocouple junction near the signal wire. In one alternative, the signal wire can be fabricated of two dissimilar metals to provide a thermocouple junction. To minimize RF noise, the RF signal may be pulsed rather than continuous, to provide time for recording thermocouple temperatures. Alternatively, a resistive heating element can be caused to produce heat when a direct or RF current is transmitted.

FIG. 13 shows a split wall graft 122 (planar configuration) with a heating element composed of several thin film resistive heaters 124 in strip form. As seen in FIG. 14, the thin film heaters can be configured by depositing metal conductive lines 126 on a polyimide or another dielectric substrate 128, with signal wires 130 also deposited on the graft and routed to a connector 132 for connection to an energy source. If desired, the thin film resistive strips are segmented to enable selective application of heat to specific regions of the graft.

Along with sealing the graft, the application of heat also increases the kinetics of thrombus formation in the region between the graft and vessel wall. This is thought to promote a more rapid healing of the aneurysm. The application of heat also enhances drug delivery or genetic infusion.

Once the graft edges have been sealed, the signal wires are removed from the graft by delivering a direct current through the wires of sufficient amplitude to cause a breakdown of each wire. The breakdown location can be selected by producing a weak point of decreased signal wire diameter. Alternatively, signal wires may be cleaved by a sharp edge supported by the delivery catheter, near the distal end. After severance, the signal wires are removed from the vasculature. As a further alternative, a sufficiently thin neck portion can allow a mechanical severance of the signal wire. In any event, since severance exposes the signal wire to the blood stream, the wire must be formed of a biocompatible material.

Figure 15:
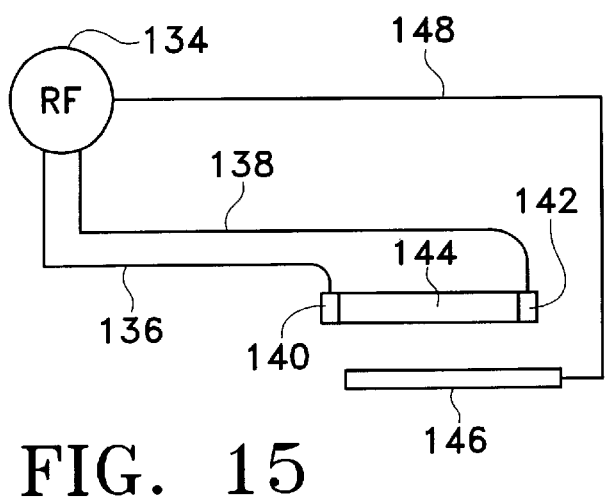
FIG. 15 is a schematic illustration of a circuit for providing electrical current to the heating elements.

FIG. 15 schematically illustrates a circuit for administering RF energy. An RF current source 134, located outside the patient, is coupled to a pair of signal wires 136 and 138, each of which is coupled to one of the two heating elements 140 and 142 at opposite ends of a graft 144. An indifferent or ground electrode 146, typically positioned along a patient's back or other appropriate location outside the body but near the location of implant, is coupled to the power source through a conductive line 148. The potential difference between the heating elements and the indifferent electrode causes ohmic heating of tissue adjacent to the heating elements.

Figure 16:
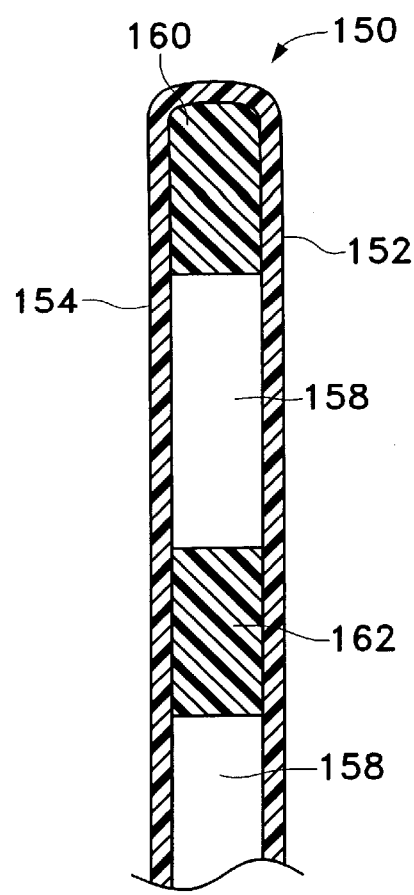
FIG. 16 is a sectional view showing a portion of a graft with two layers of graft material to provide a pocket.

FIG. 16 is a sectional view showing a graft 150 in which two graft material layers, indicated at 152 and 154, are provided on opposite sides of a structural layer 156. This construction forms a pocket 158 between spaced apart sections 160 and 162 of the structural layer. The pocket can be loaded with a drug solution, which after implantation is allowed to diffuse into the target vessel over time. Examples of suitable drug solutions are fibrinogen adhesives to aid bonding to the vessel wall, heparin to decrease the acute thrombogenisity of the graft material, pharmacological agents (urokinase, TPA, or streptokinase) to lyse thrombi, collagen to promote formation of an endothelial layer, glycerol to increase the radiopacity of the graft material, and tissue plasminogen activators. Alternatively a radiopaque contrast material can be provided for better visualization of the graft.

To control the diffusion of the drug solution or other material, outer graft layer 152 can be constructed of a material having a high porosity, while inner graft layer 154 can be fabricated of a relatively nonporous material. Different pockets may contain different solutions with different functions. A drug solution may be introduced into the graft through piercing with a small gauge needle through the graft material and injecting the drug solution directly into the pockets. As an alternative, a homeostatic valve constructed of silicone or other elastomer may be included in the inside graft material layer. The graft material also may be impregnated or filled with drug solutions using a vacuum process. While the graft is submerged in a drug solution, a vacuum is applied to draw the drug solution into the graft.

It is thought that the use of heating elements to seal the graft also increases diffusion kinetics by causing reversible poration of the cell membranes, to enhance introduction of a drug or genetic solution into the vessel wall or blood stream. Relatively large amplitude pulses of d.c. or RF energy can be used to cause electroporation of cell membranes within the vessel wall. Delivery can be highly localized, significantly reducing required amounts as compared to a systemic dosing.

The pockets facilitate an alternative approach to maintaining an implanted graft in a desired radially-enlarged profile. Specifically, biocompatible foam or adhesives can be provided in the pockets between the graft material layers. These foams or adhesives solidify as they cure, and tend to maintain the graft shape. This facilitates the forming of non-uniform graft shapes as the graft is positioned at the treatment site, and is particularly useful when the graft is positioned in a branching vessel. In some cases, the graft can be heated to reduce curing time. Alternatively, ultraviolet light or other light can be used to cure the adhesives.

Figure 17:
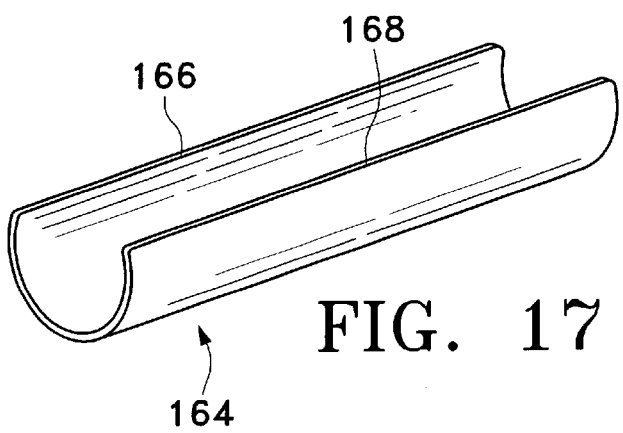
FIG. 17 is a perspective view of a further alternative graft.
Figure 18:
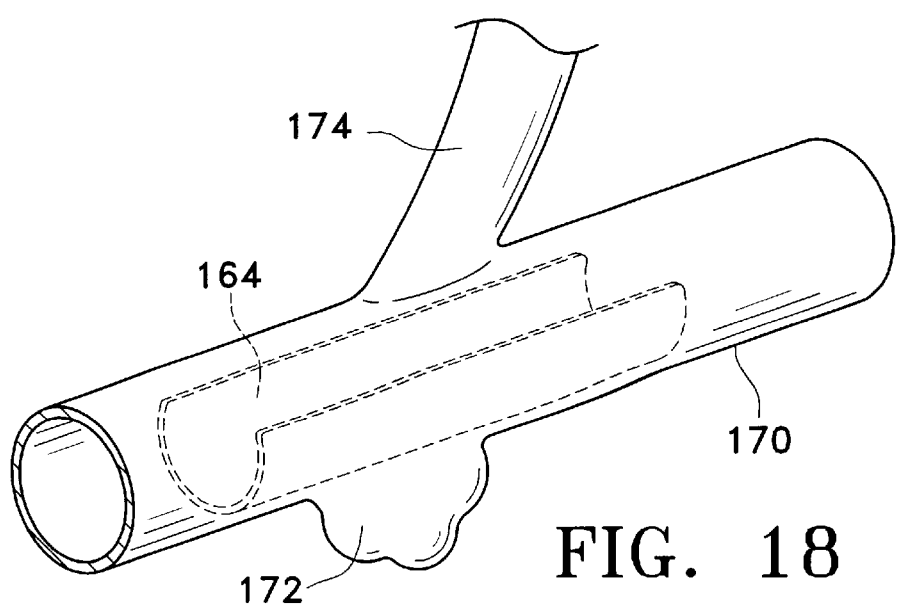
FIG. 18 shows the graft of FIG. 17 deployed in a vessel.
Figure 19:
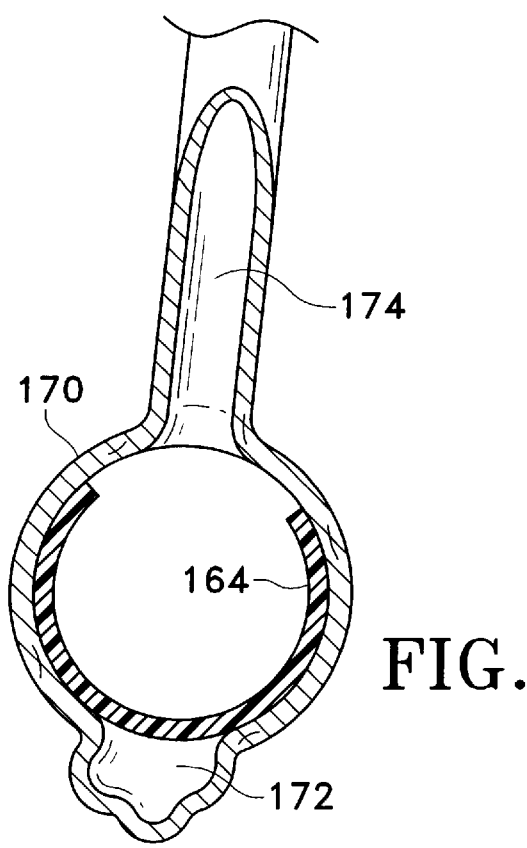
FIG. 19 is a sectional view of the graft and vessel in FIG. 18.

FIG. 17 shows an implantable graft 164 formed with a layer and a graft material layer and thermally shaped into a generally tubular shape. Graft 164 differs from previously described grafts in that it does not form a complete circumferential closure when in the relaxed state, nor when implanted. Rather, the graft has two axial edges 166 and 168 that remain spaced apart. As seen in FIGS. 18 and 19, graft 164 is implanted within a vessel 170 having an aneurysm 172 that is localized in the sense that it does not circumferentially surround the vessel. A side branch 174 is open to vessel 170, circumferentially spaced apart from the aneurysm. The split wall graft is positioned to isolate the aneurysm from the blood flow, while at the same time the gap between axial edges 166 and 168 is aligned with side branch 174, to maintain its patency. This graft is suitable for treating dissecting aneurysms where a target fissure may be located. The graft, when expanded radially to the relaxed state, should have a circumferential extent greater than 180 degrees to insure intimate contact with the vessel wall.

Figure 20:
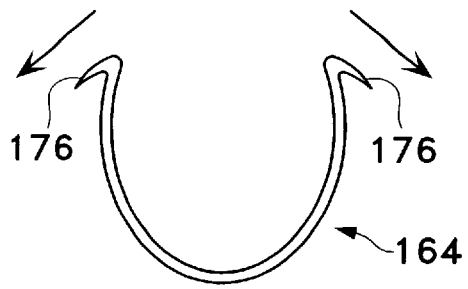
FIG. 20 is a sectional view of an alternative graft similar to the graft in FIG. 17.

As seen in FIG. 20, the ends of this type of graft can be provided with hooks 176 to enhance graft fixation, and particular to prevent circumferential shifting. Further, heating elements can be provided for thermal bonding.

Figure 21:
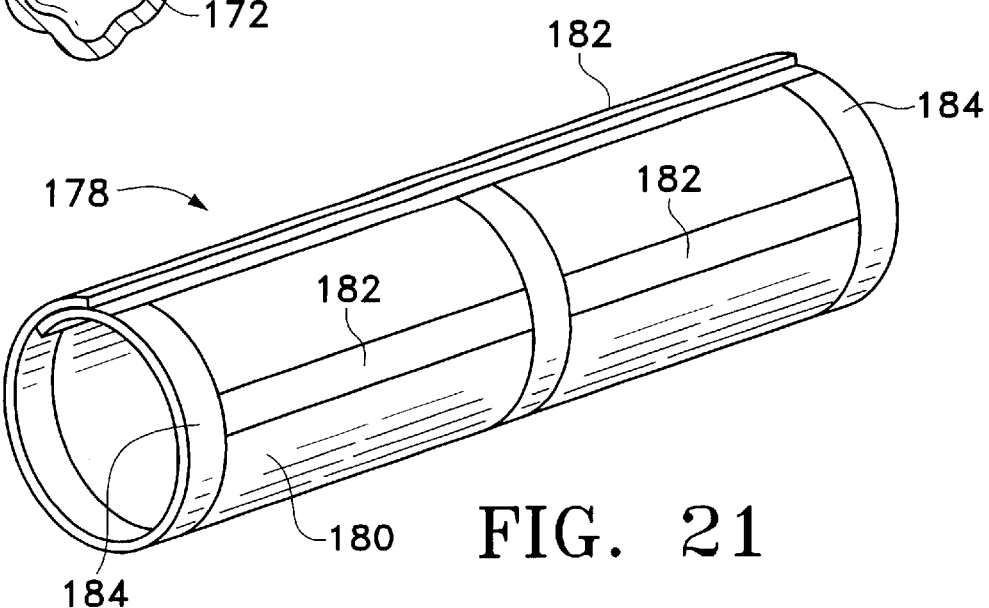
FIG. 21 is a perspective view of a further alternative graft.
Figure 22:
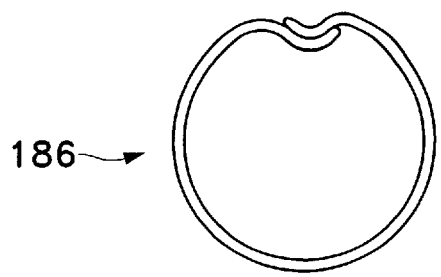
FIG. 22 is an end view of the graft in FIG. 21 illustrating interlocking structural members.

Another alternative embodiment graft 178, shown in FIGS. 21 and 22, includes a graft material layer 180 secured to a support structure that includes axial members 182 along the axial edges and at intermediate locations, and circumferential members 184. Graft 178, like the previously discussed grafts, is radially collapsed by winding it into a tighter coil or scroll. The opposed axial ends can overlap one another as previously described. Alternatively, as seen in FIG. 22, circumferential support members 186 near the axial ends can be shaped to provide an interlocking of the graft in a selected profile, to augment the elastic restoring force.

Figure 23:
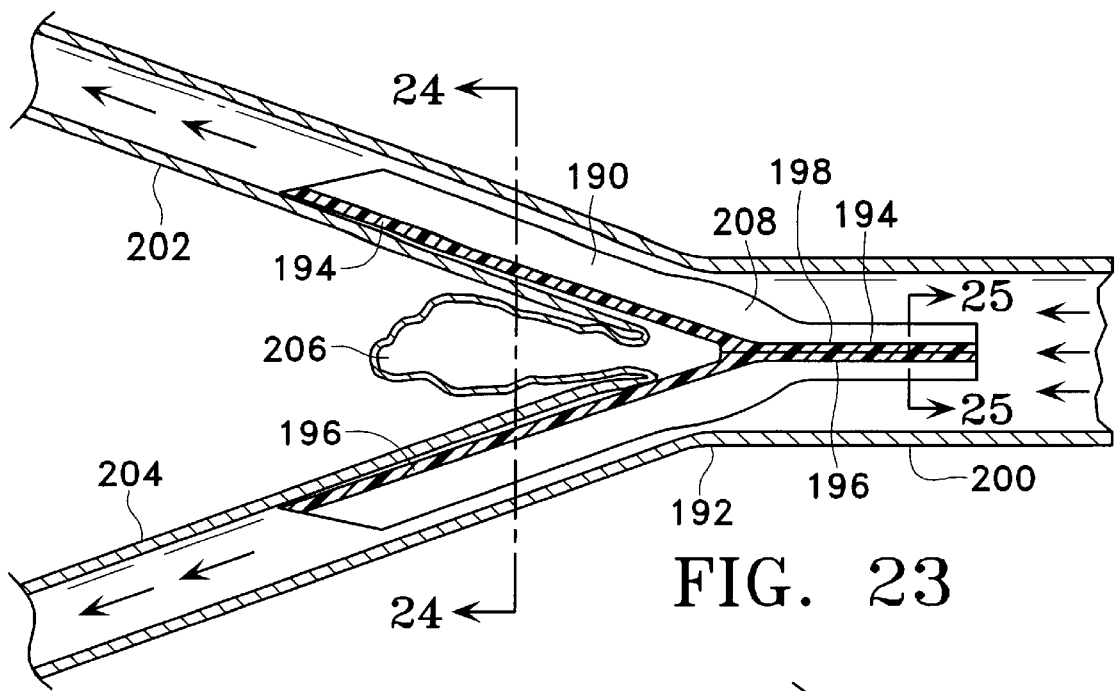
FIG. 23 is a side elevation of a bifurcated graft, formed according to the present invention, deployed within a vessel.
Figure 24:
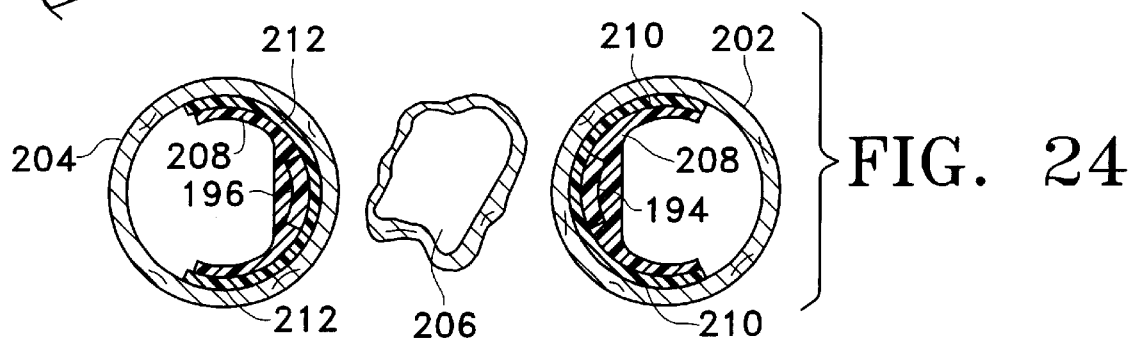
FIG. 24 is a sectional view taken along the line 24—24 in FIG. 23.
Figure 25:
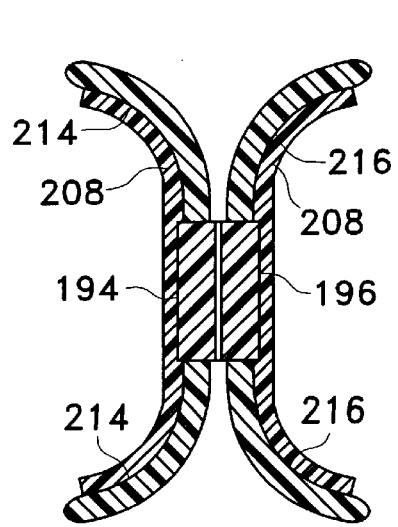
FIG. 25 is a sectional view taken along the line 25—25 in FIG. 23.

FIG. 23 shows a further embodiment, namely a bifurcated graft 190 implanted in a branched vessel 192, e.g., where the abdominal aorta branches into the iliac arteries. Graft 190 includes two structural layers with respective primary sections 194 and 196. Over a portion of their lengths, the primary sections are joined together to provide a main stem 198 of the support structure implanted in a main vessel 200. Over the rest of their lengths, the primary sections are separated from one another at an angle, so that the structural layers in section resemble the letter "Y." Each primary section extends into a different one of branching vessels 202 and 204. An aneurysm 206, formed at the junction of the main and branching vessels, thus is isolated from the blood flow by a graft material layer 208 attached to the primary sections and to secondary sections (not shown in FIG. 23) that extend transversely and arcuately from the primary section, as in the tubular grafts previously described. FIGS. 24 and 25 are sectional views, taken along the graft stem portion and branching portions, respectively, illustrating the extension of secondary sections 210–216 from their respective primary sections. The angle between primary sections 194 and 196 when graft 190 is in the relaxed state can be configured to provide an elastic restoring force against branching vessels 202 and 204, to help maintain the graft in place.

Figure 26:
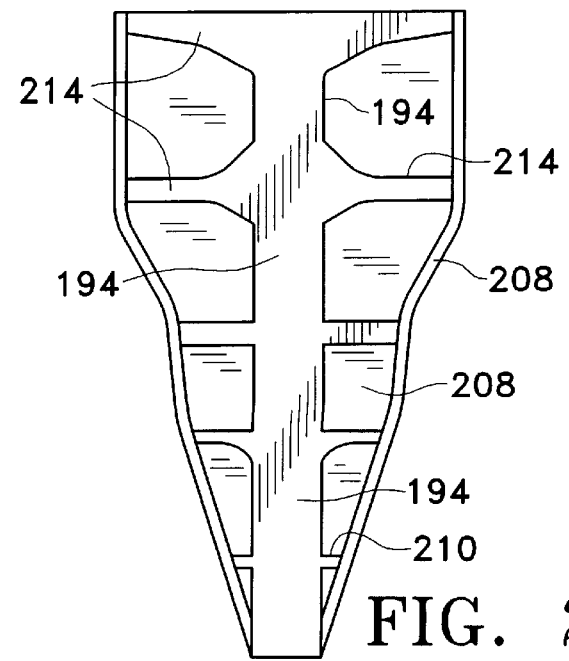
FIG. 26 is a plan view of part of the graft.

Each of the structural layers, including the associated longitudinal primary section and transverse secondary sections, can be fabricated initially by stamping them from a flat sheet for a planar configuration as seen in FIG. 26, then later thermally shaping them to the desired radius. As shown, graft material layer 208 is secured to the free ends of the secondary sections and can be bonded to the support structure at other locations if desired. Suitable modifications include providing branching portions of the graft with unequal lengths to account for non-uniform branching vessels or to limit advancement of one of the branching legs. The angle between branching legs in the relaxed state also can be selected to fit different vessels. The ribs or secondary sections can be tapered as shown to vary the restoring force against the vessel wall, and rib thickness likewise can be varied.

Figure 27:
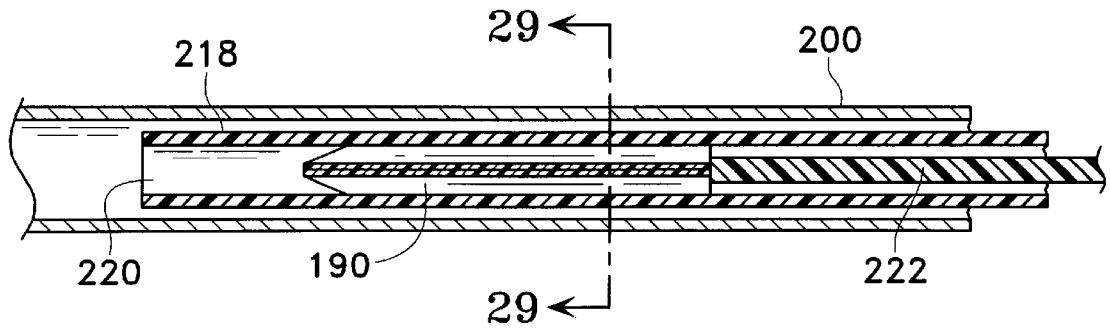
FIGS. 27 and 28 are side sectional views of an alternative bifurcated graft and system for deploying the graft in a vessel.
Figure 28:
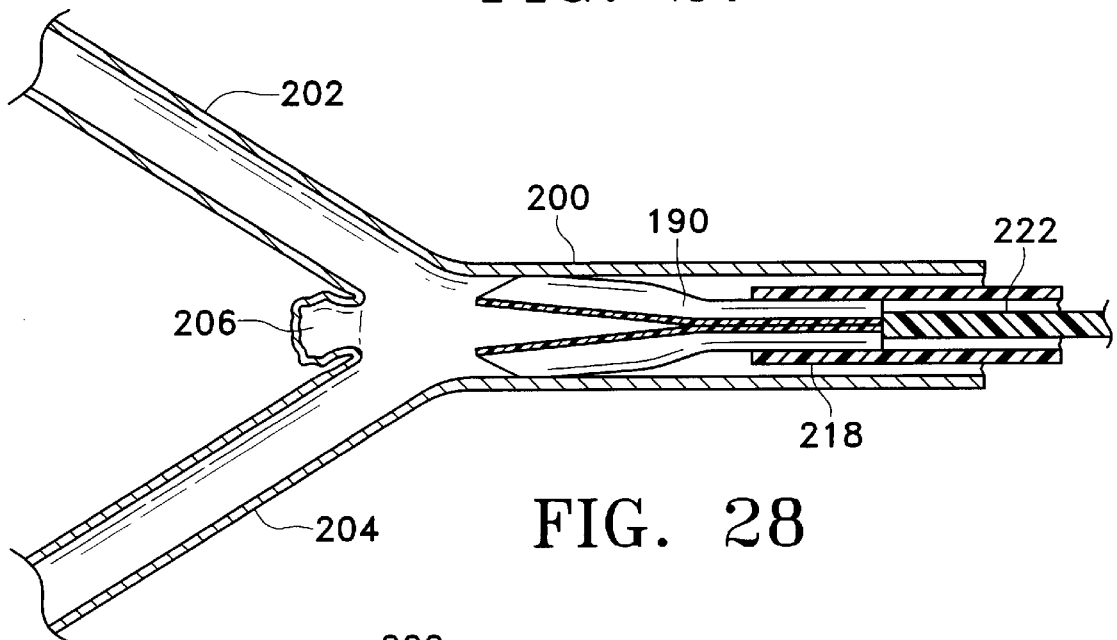
Figure 29:
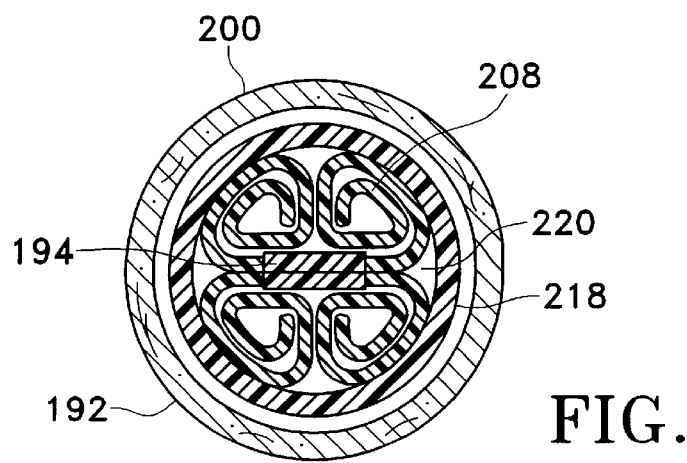
FIG. 29 is a sectional view taken along the line 29—29 in FIG. 27.

FIGS. 27 through 29 show a system for deploying graft 190, including a catheter 218 with a lumen 220 for containing the graft and a stylet 222 axially movable within the lumen, to abut a proximal end of the graft and advance the graft distally beyond the catheter, allowing the branching legs to separate from one another and also allowing radial expansion along the branches and the proximal stem where the primary sections are connected.

FIGS. 30 and 31 show an alternative deployment system in which catheter lumen 220 also contains a pair of wires 224 and 226 coupled to the distal ends of primary sections 194 and 196, respectively. The wires are anchored by hooks or rivets 228 inserted through the graft material layer.

Figure 33:
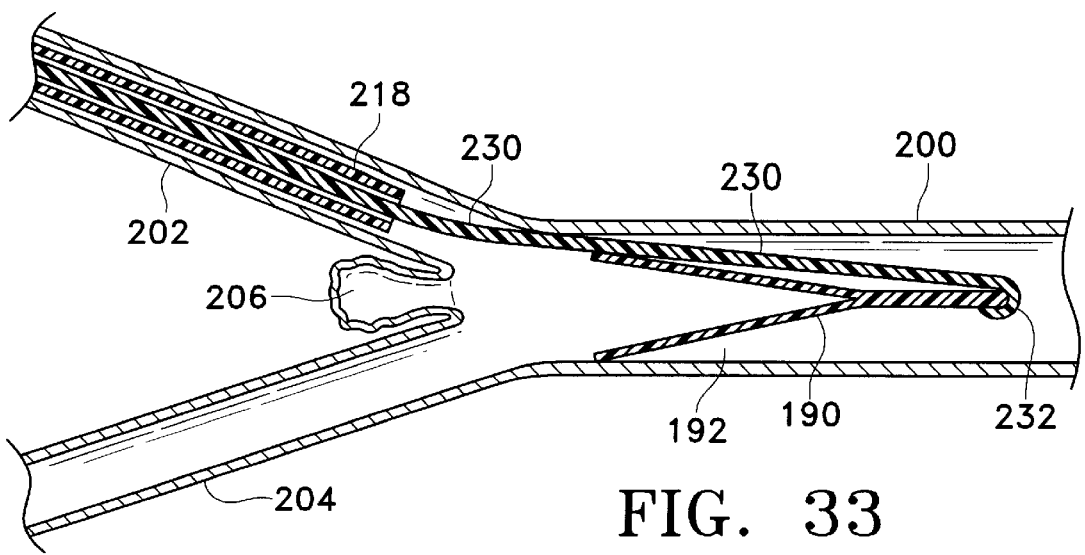
FIG. 33 shows use of an alternative deployment system to position the graft of FIG. 30 in a branched vessel.

FIGS. 32 and 33 illustrate another alternative deployment approach in which the catheter is advanced through one of the branching vessels toward the main vessel. A stylet 230 includes a hooked end 232 for moving the graft proximally, i.e., toward the branching vessels as viewed in FIG. 33, as the stylet is moved proximally.

Figure 34:
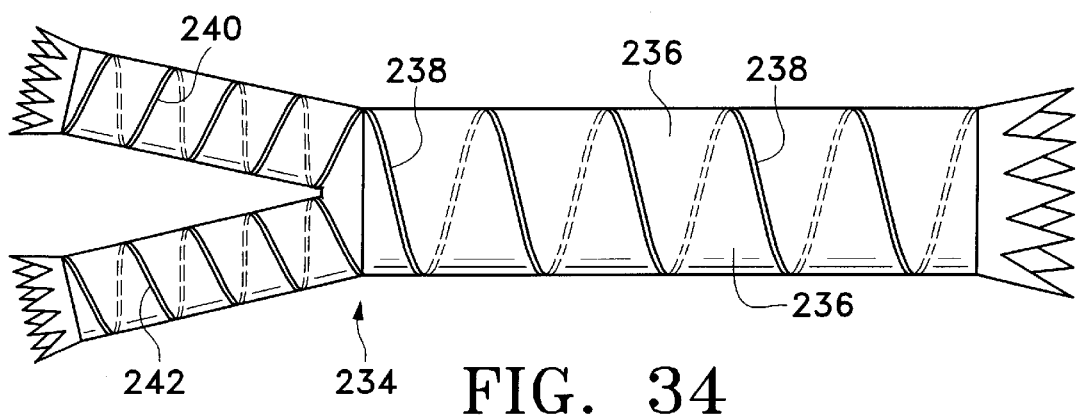
FIG. 34 illustrates an alternative embodiment bifurcated graft.

FIG. 34 illustrates an alternative bifurcated graft 234 in which a graft material layer 236 is supported by coiled support members 238, 240 and 242.

Figure 35:
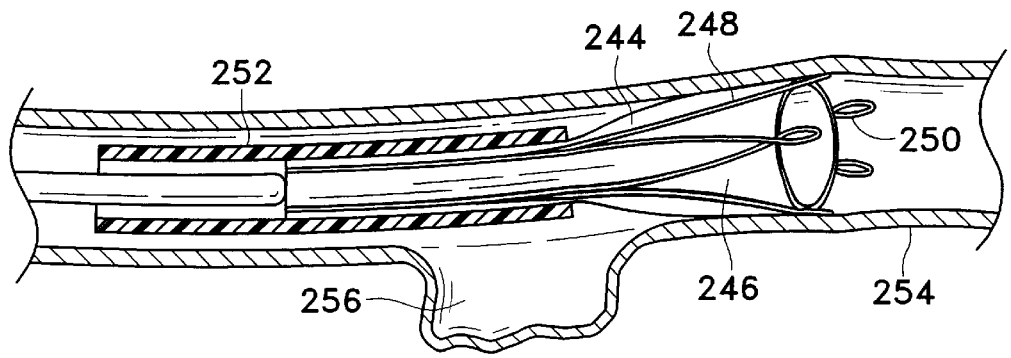
FIG. 35 illustrates a further alternative graft contained within a catheter distal end and positioned in a vessel.
Figure 36:
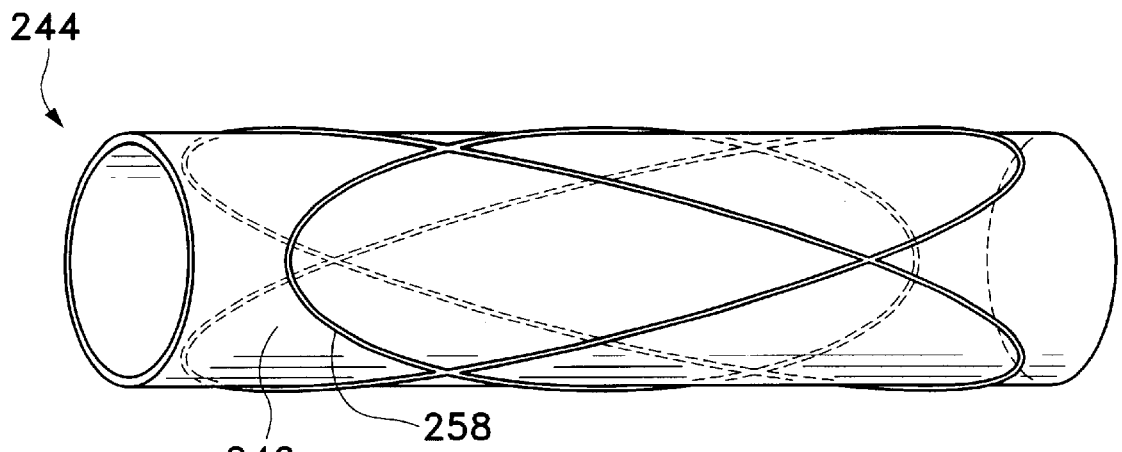
FIGS. 36–38 illustrate alternative support structures for cylindrical grafts.
Figure 38:
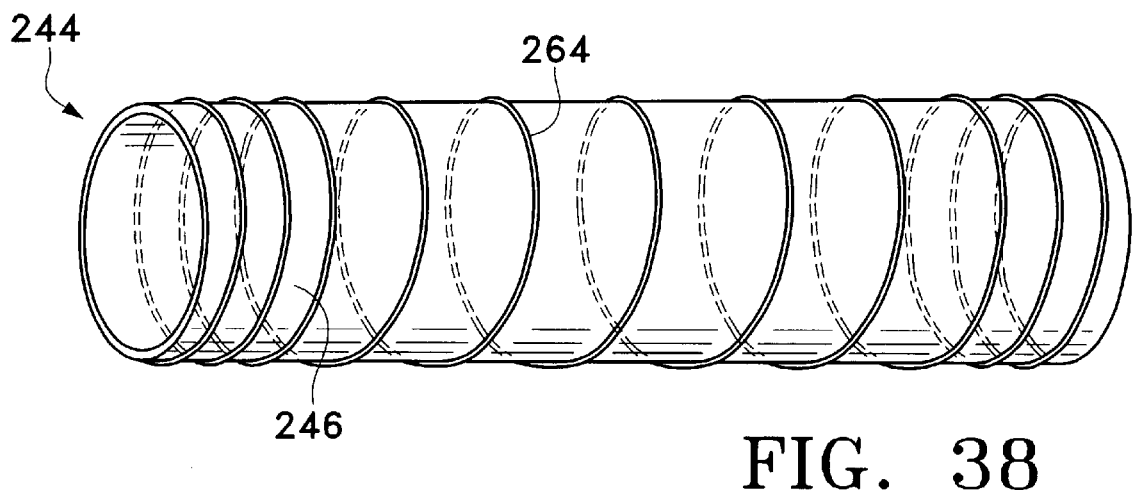
Figure 44A:
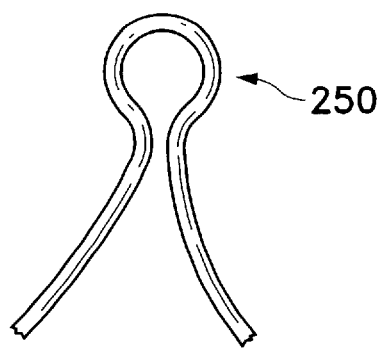
Figure 44B:
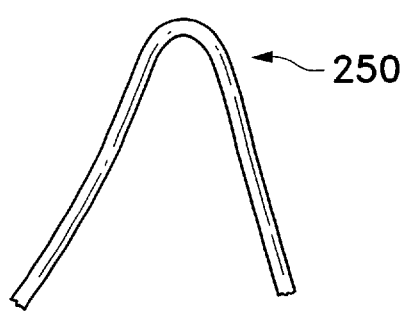
Figure 44C:
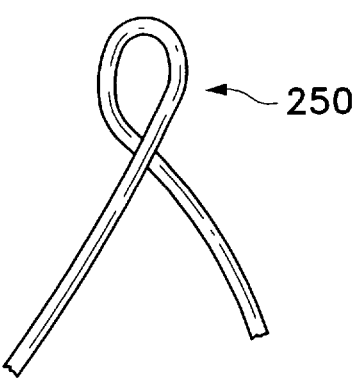
Figure 44D:
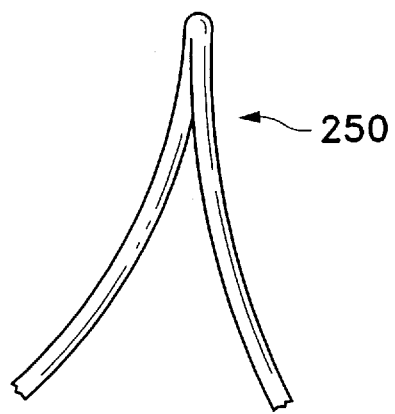

FIG. 35 shows an implantable graft 244 of continuous rather than split end form, including a graft material layer 246 and a support structure 248 with looped terminal ends 250 that extend beyond the graft material. The graft is shown partially deployed from a catheter 252 within a vessel 254 having an aneurysm 256. FIGS. 36–38 show alternative support structure arrangements, including a series of elliptical loops 258 in FIG. 36, a continuous strand forming longitudinal extensions 260 and loops 262 joining adjacent longitudinal members in FIG. 37, and a helical or coiled arrangement of a single strand 264 in FIG. 38. The pitch between adjacent helical windings varies, with substantially closer spacing between adjacent turns of the coil near the graft ends, to provide more positive support (elastic radial expansion) against the vessel wall.

FIGS. 39–43 illustrate a variety of approaches to joining the support structure and graft material, including bonding the graft material 246 to itself when it surrounds the supporting strand 258 as in FIGS. 39 and 40. The support members 262 can be laminated in the graft material, as shown in FIG. 41. Support strands wound about in initial graft layer can be dipped in future graft material to achieve this result. Separate layers of graft material can be bonded together about a support strand, as shown in FIG. 42. Finally, the graft material 246 and strands 262 can be interwoven, as shown in FIG. 43.

The terminal ends 250 of the support strands can be shaped in a variety of ways, as seen in FIGS. 44a–d. The longitudinal strand arrangement of FIG. 37 can have outwardly flared end loops, as indicated in FIG. 45. FIG. 46 shows the loop of FIG. 44c partially extended beyond the graft material.

FIGS. 47 and 48 show a system for deploying graft 244, including a catheter 266 having a lumen 268, a stylet 270 contained within the lumen and moveable axially relative to the catheter, and a suture 272, contained within the stylet and further threaded through the terminal ends 250 of the graft. As indicated, pulling the suture proximally brings the terminal ends together, thus radially reducing graft 244 at least near its proximal end. This feature enables a radial reduction and repositioning of a partially deployed graft.

FIGS. 49–51 show a further alternative embodiment graft 274 and a mechanism for deploying the graft. Graft 274 includes a cylindrical graft material layer 276, and four generally axial and circumferentially spaced apart elongate support members 278–284. The support members are flat and have a sinusoidal curvature as seen in connection with members 278 and 282 in FIG. 49. As best seen in FIG. 50, the curvature is reduced when opposite ends of the graft are pulled further axially apart from one another.

The axial distance between the opposite graft ends is controlled by a pair of stylets 286 and 288. As seen in FIGS. 52 and 53, interior stylet 286 is coupled to the distal end of the graft through hooks 290, and outer stylet 288 is coupled to the proximal graft end through hooks 292. Stylet 286 is moveable axially relative to stylet 288, to adjust the distance between the opposite graft ends, and thus also adjust the graft radius.

FIGS. 54–56 show a graft 294 consisting of a graft material layer 296, i.e., having no rib cage or other support structure. Graft 294 is formed of a resilient elastomer, woven or otherwise formed into walls sufficiently thick to provide a residual force that radially expands the graft into intimate contact with surrounding blood vessel tissue. At the same time, porosily is sufficiently low to isolate an aneurysm or other vessel abnormality. The opposite ends of the graft can be flared radially outward as indicated at 298, to more positively prevent leakage between the graft and vessel wall, and to prevent axial motion of the implanted graft. The elastic graft is readily collapsed by folding and stretching, into the reduced profile shown in FIG. 56. The graft can be deployed by one of the previously described systems.

Thus, in accordance with the present invention, a prosthesis is formable elastically into a reduced-radius profile, and expands radially at the implant site to establish firm contact against tissue. The grafts have support structures of primary and secondary sections that can be shaped to accommodate irregular vessels or to provide residual force gradients. Grafts constructed of resilient material, and not requiring separate support structures, can accommodate narrower vessels.

What is claimed is:

1. An intralumenally implantable prosthesis including:

a structural layer including a single elongate primary section extended in a longitudinal direction, the structural layer further including a plurality of secondary sections extended substantially transversally from the primary section and curved about an axis substantially parallel to the primary section, whereby the structural layer is thermally set so to conform, when in a substantially relaxed and fully deployed state, to a cylindrical shape having a predetermined radius, wherein the secondary sections are flexible to allow a radial reduction of the structural layer to a reduced-radius delivery profile responsive to an external force, and wherein the structural layer requires a continued application of the external force to maintain the reduced-radius delivery profile and alternatively tends to return to the substantially relaxed and fully deployed state upon removal of the external force; and a substantially continuous and compliant graft layer, supported by the structural layer, tending to conform to the shape of the structural layer, and substantially impervious to blood.

2. The prosthesis of claim 1 wherein:

each of the secondary sections converges in profile in a direction from a first end of the secondary segment adjacent the primary segment toward a second and opposite end of the secondary section.

3. The prosthesis of claim 1 wherein:

the structural layer when in the delivery profile is positionable at a treatment site along a tissue wall defining a body lumen, and radially expands into contact with the tissue wall segment upon release of the external force.

4. The prosthesis of claim 3 further including:

a heating component for heating at least a portion of the tissue near the treatment site while the support structure is in contact with the tissue wall.

5. The prosthesis of claim 4 wherein:

the heating means comprises at least one electrical heating element mounted adjacent the structural layer, and a means for providing an electrical current to the heating element to thermally bond the structural layer to the tissue wall segment.

6. The prosthesis of claim 1 wherein:

said secondary sections extend from opposite sides of the primary section, and opposed ones of the secondary sections overlap one another when the structural layer is in the relaxed state.

7. The prosthesis of claim 1 wherein:

the secondary members extend from opposite sides of the primary section, and respective ends of opposed second sections are spaced apart from one another when the structural layer is in the relaxed state.

8. The prosthesis of claim 1 additionally comprising:

an elongate and flexible delivery device having a proximal end and a distal end, intravascularly insertable by its distal end, to position the distal end at an intralumenal site while the proximal end remains outside of the body;

said delivery device including a prosthesis confining structure near the distal end of the device, for applying the external force to maintain the structural layer in the reduced-radius delivery profile; and a control component operable from the proximal end of the device, for removing the external force to allow the structural layer to radially expand into contact with tissue at the site.

9. The system of claim 8 wherein:

the delivery device is a catheter, the confining structure includes a catheter wall defining a lumen extending at least along the distal end of the catheter and adapted to maintain the structural layer in the delivery state; and the control component includes a means for moving the structural layer distally relative to the catheter, beyond the distal end to allow the structural layer to radially expand.

10. The system of claim 9 wherein:

the moving means includes a stylet adapted to engage a proximal end of the structural layer and either (i) move the structural layer distally while the catheter remains stationary; or (ii) maintain the structural layer stationary while the catheter is proximately withdrawn.

11. The prosthesis of claim 1 further including:

a second substantially continuous and compliant graft layer supported by the structural layer, disposed adjacent the first graft layer and cooperating with the first graft layer to form at least one pocket containing at least one of: a drug solution for diffusion into the tissue; and a biocompatible foam adapted to solidify after said expansion into contact with the tissue.

12. The graft of claim 11 additionally comprising:

an elongate and flexible delivery device having a proximal end and a distal end, intravascularly insertable by its distal end, to position the distal end at an intralumenal site while the proximal end remains outside of the body;

said delivery device including first and second elongate stylets near the distal end of the device for applying the external force to maintain the structural layer in the reduced-radius delivery profile, the stylets being releasably coupled to proximal and distal ends of the structural layer, respectively; the stylets being axially movable relative to one another so to axially elongate the structural layer and radially reduce the structural layer to the delivery profile; the stylets additionally being axially movable to allow the structural layer to radially expand; and a control component operable from the proximal end of the device for removing the external force to allow the structural layer to radially expand into contact with tissue at the site.

13. An intravascularly implantable graft, including:

a tubular graft body consisting essentially of an elastomer and self-supporting to have a predetermined radius when in a substantially relaxed and fully deployed state, said graft body having a continuous tubular wall substantially impervious to blood and other body fluids, said body being collapsible into a reduced-radius profile responsive to the application of an external force, and resiliently returning toward the substantially relaxed, fully deployed state upon removal of the external force.

14. The prosthesis of claim 13 wherein:

the graft body includes opposite flared end regions, each having a radius larger than the predetermined radius when the graft body is in the relaxed state.

15. An intraluminally implantable prosthesis, including:

a structural layer forming a framework curved about an axis and having a predetermined radius when in a relaxed state, adapted to undergo a radial compression to a reduced-radius delivery profile responsive to an external force, and tending to return to the relaxed state upon removal of the external force, said structural layer when in the delivery profile being positionable at a treatment site along a tissue wall defining a body lumen and adapted to radially expand into contact with the tissue wall segment upon release of the external force; and a heating element supported by the structural layer, adapted for heating at least a portion of the tissue wall segment contiguous with the structural layer sufficiently to thermally bond the structural layer with respect to said portion of the tissue wall segment.

16. The prosthesis of claim 15 further including:

a means for providing an electrical current to the heating element to effect said heating, wherein the heating element is electrically conductive.

17. The prosthesis of claim 16 wherein:

the heating element comprises a plurality of elongate electrode strips fixed with respect to the structural layer, and disposed radially outward thereof.

18. The prosthesis of claim 16 further including:

an indifferent electrode coupled to the current source, said current source being an RF current source, wherein the indifferent electrode is positionable in spaced apart relation to the heating element.

19. The prosthesis of claim 16 further including:

a substantially continuous and compliant graft layer, supported by the structural layer, tending to conform to the shape of the structural layer, and substantially impervious to blood and other body fluids.

20. The prosthesis of claim 15 wherein:

the structural layer includes at least one elongate primary section extended in a direction parallel to the axis, and further includes a plurality of secondary sections extended substantially transversally from the at least one primary section and curved about the axis.

21. An intraluminal implantable graft including:

a compliant tubular body defining a lumen and having first and second ends;

a support structure attached to the tubular body, defining the shape of the tubular body, and having first and second support portions at the first and second ends, respectively; and an electrode structure attached to the tubular body and having first and second electrode portions at the first and second ends, respectively.

22. The graft of claim 21 wherein:

said portions of the support structure are electrically conductive and provide said electrode portions.

23. The graft of claim 21 wherein:

the support structure is adapted to assume a delivery profile responsive to application of an external force to facilitate an intraluminal positioning thereof along a tissue wall defining a body lumen, and is radially expandable into contact with the tissue wall upon release of the external force.

24. The graft of claim 23 wherein:

the electrode structure is adapted to heat the tissue wall while the support structure is in contact therewith.

25. The graft of claim 23 wherein:

the electrode structure comprises at least one electrical heating element mounted adjacent the support structure, and a means for transmitting an electrical current to the heating element to facilitate a thermal securement of the tubular body and support structure to the tissue wall.

26. The graft of claim 21 wherein:

the tubular body includes at least two compliant graft layers supported by the support structure; and the at least two compliant graft layers form at least one pocket adapted to contain at least one of: a solution adapted for treatment of tissue at the treatment site; an adhesive solution for enhancing bonding of the tubular body to tissue at the treatment site; and a biocompatible, curable foam.

27. The graft of claim 26 wherein:

the at least two compliant graft layers have different porosities.

28. The graft of claim 27 wherein:

the at least two compliant graft layers comprise a substantially non-porous inner graft layer, and a substantially porous outer graft layer, thereby facilitating a selective diffusion of a solution contained in the at least one pocket at least primarily in the outward direction.

29. The graft of claim 26 wherein:

said at least one pocket is adapted to contain said solution for diffusion to the tissue at the treatment site, and said electrode structure includes an electrical element and means for transmitting an electrical current to the electrical element with an amplitude sufficient to cause electroporation of the tissue adjacent the electrical element.

30. The system of claim 26 wherein:

said power source is adapted to provide to the at least one electrode an electrical current of sufficient amplitude to cause electroporation of the tissue adjacent the at least one electrode.

31. A system for securing an implantable graft to a vessel, including:

a compliant graft;

at least one support structure attached to and supporting the graft;

at least one electrode attached to the graft adjacent the at least one support structure;

at least one electrical conductor;

a power source for providing an electrical current to the at least one electrode via the conductor sufficient to heat tissue adjacent the at least one electrode to thermally secure the graft and support structure with respect to said tissue; and an electrical coupling of the conductor with the at least one electrode, adapted to facilitate a separation of the conductor from the at least one electrode after the graft and support structure have been so secured.

32. The system of claim 31 wherein:

the support structure comprises the electrode structure.

33. The system of claim 31 wherein:

the support structure is adapted to assume a delivery profile to facilitate deployment of the support structure and graft to a treatment site along a tissue wall defining a body lumen, and further is radially expandable into contact with the tissue wall.

34. The system of claim 31 further including:

an indifferent electrode electrically coupled to the power source and positionable in spaced-apart relation to the at least one electrode, wherein the power source comprises an RF generator.

35. The system of claim 31 wherein:

said electrical coupling of the conductor and the at least one electrode comprises a constriction adapted to undergo a breakdown when subjected to current of a predetermined amplitude, thereby to sever the conductor from the electrode.

36. The system of claim 31 wherein:

the graft includes at least two compliant graft layers supported by the support structure and cooperating to form at least one pocket adapted to contain at least one of: a solution adapted for diffusion from the pocket to adjacent tissue to treat the adjacent tissue; an adhesive solution to promote a bonding of the graft to the tissue; and a biocompatible, curable foam.

37. An intralumenally implantable prosthesis including:

a structural layer including a single elongate primary section extended in a longitudinal direction, the structural layer further including a plurality of secondary sections extended substantially transversely from the primary section, the structural layer being thermally set so that when in a relaxed state the plurality of secondary sections are curved about an axis substantially parallel to the primary section to impart a substantially cylindrical shape to the structural layer;

wherein the structural layer self-expands from a reduced-radius delivery profile to an enlarged-radius deployment profile upon removal of an external force, wherein each of the secondary sections converges in profile in a direction from a first end of the secondary segment adjacent the primary segment toward a second and opposite end of the secondary section; and a substantially continuous and compliant graft layer, supported by the structural layer, tending to conform to the shape of the structural layer, and substantially impervious to blood.

38. The prosthesis of claim 37 wherein:

said structural layer is formed of a memory elastic material.

39. An intraluminal implantable graft including:

a self-supporting structural layer;

a first substantially continuous and compliant graft layer supported by the structural layer and tending to conform to the shape of the structural layer; and a second substantially continuous and compliant graft layer, supported by the structural layer, tending to conform to the shape of the structural layer, and cooperating with the first graft layer to form a pocket containing at least one constituent selected from the group of constituents consisting of: a solution adapted for treatment of tissue at a treatment site within a body lumen; an adhesive solution for enhancing bonding of at least one of the graft layers to tissue at the treatment site; and a biocompatible, curable foam.

40. The graft of claim 39 wherein:

one of said first and second graft layers is more porous than the other.

41. The graft of claim 39 further including:

at least one electrode attached to at least one of the first and second graft layers, and an electrical conductor electrically coupled to the at least one electrode.

42. The graft of claim 39 wherein:

the support layer is elastically deformable into a reduced-radius delivery profile responsive to application of an external force, and tends to radially enlarge upon removal of the external force.

* * * * *